United States Patent
Chafin et al.

(10) Patent No.: US 10,126,216 B2
(45) Date of Patent: Nov. 13, 2018

(54) METHOD FOR TISSUE SAMPLE FIXATION

(75) Inventors: David Chafin, Tucson, AZ (US); Abbey Pierson Theiss, Tucson, AZ (US); Michael Otter, Tucson, AZ (US); Esteban Roberts, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/372,040

(22) Filed: Feb. 13, 2012

(65) Prior Publication Data

US 2012/0214195 A1 Aug. 23, 2012

Related U.S. Application Data

(63) Continuation-in-part of application No. PCT/US2011/027284, filed on Mar. 4, 2011.

(60) Provisional application No. 61/464,479, filed on Mar. 4, 2011, provisional application No. 61/463,551, filed on Feb. 17, 2011.

(51) Int. Cl.
*G01N 1/30* (2006.01)
*G01N 1/31* (2006.01)

(52) U.S. Cl.
CPC .............. *G01N 1/30* (2013.01); *G01N 1/31* (2013.01)

(58) Field of Classification Search
None
See application file for complete search history.

(56) References Cited

U.S. PATENT DOCUMENTS

| | | |
|---|---|---|
| 3,961,097 A | 6/1976 | Gravlee, Jr. |
| 4,275,149 A | 6/1981 | Litman et al. |
| 4,318,980 A | 3/1982 | Boguslaski et al. |
| 4,495,817 A | 1/1985 | Hunt et al. |
| 4,656,047 A | 4/1987 | Kok et al. |
| 4,839,194 A | 6/1989 | Malluche et al. |
| 4,891,239 A | 1/1990 | Dudley et al. |
| 5,089,288 A | 2/1992 | Berger |
| 5,197,475 A | 3/1993 | Antich et al. |
| 5,523,204 A | 6/1996 | Singer et al. |
| 5,595,707 A | 1/1997 | Copeland et al. |
| 5,639,423 A | 6/1997 | Northrup et al. |
| 5,654,200 A | 8/1997 | Copeland et al. |
| 5,665,141 A | 9/1997 | Vago |
| 5,983,723 A | 11/1999 | Buckin et al. |
| 5,984,881 A | 11/1999 | Ishibashi et al. |
| 6,004,762 A | 12/1999 | Tse et al. |
| 6,042,874 A | 3/2000 | Visinoni et al. |
| 6,207,408 B1 | 3/2001 | Essenfeld et al. |
| 6,291,180 B1 | 9/2001 | Chu |
| 6,296,809 B1 | 10/2001 | Richards et al. |
| 6,352,861 B1 | 3/2002 | Copeland et al. |
| 6,582,962 B1 | 6/2003 | Richards et al. |
| 6,586,713 B2 | 7/2003 | Essenfeld et al. |
| 6,746,848 B2 | 6/2004 | Smith |
| 6,793,890 B2 | 9/2004 | Morales et al. |
| 6,875,583 B2 | 4/2005 | Giberson et al. |
| 7,075,045 B2 | 7/2006 | Visinoni |
| 7,090,974 B2 | 8/2006 | Chu |
| 7,262,022 B2 | 8/2007 | Chu |
| 7,300,439 B2 | 11/2007 | May |
| 7,666,620 B2 | 2/2010 | Wiederhold |
| 7,687,255 B2 | 3/2010 | Chu |
| 7,767,434 B2 | 8/2010 | Chu |
| 2002/0177183 A1 | 11/2002 | Giberson et al. |
| 2003/0197008 A1 | 10/2003 | Giberson et al. |
| 2004/0029184 A1 | 2/2004 | Gourevitch |
| 2004/0267263 A1 | 12/2004 | May |
| 2005/0269315 A1 | 12/2005 | Visinoni et al. |
| 2007/0072258 A1* | 3/2007 | Chu .......................... 435/40.5 |
| 2008/0102006 A1 | 5/2008 | Kram et al. |

(Continued)

FOREIGN PATENT DOCUMENTS

| | | |
|---|---|---|
| CN | 1310797 A | 8/2001 |
| CN | 101636649 A | 1/2010 |

(Continued)

OTHER PUBLICATIONS

Srinivasan et al. (American Journal of Pathology, vol. 161, No. 6, p. 1961-1971, 2002).*
Bowe et al. (Molecular and Cellular Biology, vol. 26, No. 22, p. 8539-8550, 2006).*
Quiring et al. (Mechanisms of Development, vol. 121, p. 971-976, 2004).*
Moens et al. (Cold Spring Harbor Protocols, 2008).*
Murphy et al. (Clinical Cancer Research, vol. 10, p. 1354-1359, 2004).*
Silahtaroglu et al. (Nature, vol. 2, No. 10, p. 2520-2528, 2007).*
Fox et al., Formaldehyde Fixation, The Journal of Histochemistry and Cytochemistry, vol. 33, No. 8, pp. 845-853, 1985.*
International Searching Authority, International Search Report, counterpart PCT Application PCT/US2011/027284, mailed Jul. 1, 2011, 3 pages.

(Continued)

*Primary Examiner* — Taeyoon Kim
*Assistant Examiner* — Srikanth Patury
(74) *Attorney, Agent, or Firm* — Thomas M. Finetti; Charney IP Law LLC

(57) ABSTRACT

An aldehyde fixative solution at a first temperature is caused to contact a tissue sample for a first time period, additionally an aldehyde fixative solution is caused to contact the tissue sample at a second temperature higher than the first temperature for a second time period. The first time period typically ranges from about 15 minutes up to about 4 hours, and the first temperature typically is from greater than 0° C. to at least 15° C. The second temperature typically is from greater than about 22° C. to about 55° C., and the second time period ranges from about 1 hour to about 4 hours. Using this process, improved tissue morphology and IHC staining as well as superior preservation of post-translation modification signals have been accomplished in approximately 4 hours compared to 24 hours for room temperature protocols, and more even morphology and antigen preservation are observed.

15 Claims, 21 Drawing Sheets
(21 of 21 Drawing Sheet(s) Filed in Color)

(56) References Cited

U.S. PATENT DOCUMENTS

| | | | |
|---|---|---|---|
| 2008/0108043 | A1 | 5/2008 | Wiederhold |
| 2008/0188767 | A1 | 8/2008 | Oaki et al. |
| 2008/0221449 | A1 | 9/2008 | Sato |
| 2009/0226059 | A1 | 9/2009 | Levenson et al. |
| 2010/0136652 | A1 | 6/2010 | Bieniarz et al. |
| 2010/0182877 | A1 | 7/2010 | Chu et al. |
| 2010/0184087 | A1 | 7/2010 | Kosmeder et al. |
| 2011/0287475 | A1 | 11/2011 | Ardekani et al. |
| 2011/0311123 | A1 | 12/2011 | Gholap et al. |
| 2012/0129169 | A1 | 5/2012 | Giovanni et al. |
| 2012/0270293 | A1* | 10/2012 | Chu .................... A01N 1/0284 435/173.5 |
| 2012/0329088 | A1 | 12/2012 | Otter et al. |
| 2013/0224791 | A1 | 8/2013 | Taft et al. |
| 2014/0186858 | A1 | 7/2014 | Van Agthoven |

FOREIGN PATENT DOCUMENTS

| | | |
|---|---|---|
| DE | 10146323 A1 | 4/2003 |
| EP | 0660930 B1 | 11/1999 |
| EP | 1410811 A1 | 4/2004 |
| EP | 1605243 A1 | 12/2005 |
| EP | 1913877 A1 | 4/2008 |
| EP | 1005633 B1 | 9/2008 |
| EP | 1491156 B1 | 12/2008 |
| EP | 2278296 | 1/2011 |
| EP | 2458365 A1 | 5/2012 |
| GB | 2192712 A | 1/1988 |
| JP | 1105159 A | 4/1989 |
| JP | 2004-037215 A | 2/2004 |
| WO | 87/00004 A1 | 1/1987 |
| WO | WO-8907656 A2 | 8/1989 |
| WO | WO-9103718 A1 | 3/1991 |
| WO | WO-9207083 A1 | 4/1992 |
| WO | WO-9407139 A1 | 3/1994 |
| WO | WO-9409808 A1 | 5/1994 |
| WO | WO-9415641 A1 | 7/1994 |
| WO | WO-9506067 A1 | 3/1995 |
| WO | WO-9640506 A1 | 12/1996 |
| WO | WO-9700888 A1 | 1/1997 |
| WO | WO-9726321 A2 | 7/1997 |
| WO | WO-9736614 A1 | 10/1997 |
| WO | WO-9801335 A1 | 1/1998 |
| WO | WO-9820834 A2 | 5/1998 |
| WO | WO-9909390 A1 | 2/1999 |
| WO | WO-9953994 A1 | 10/1999 |
| WO | WO-9966947 A1 | 12/1999 |
| WO | WO-9967634 A1 | 12/1999 |
| WO | 00/00813 A1 | 1/2000 |
| WO | 0000813 A1 | 1/2000 |
| WO | 03/066560 A1 | 8/2003 |
| WO | WO-2005054811 A2 | 6/2005 |
| WO | WO-2005121773 A1 | 12/2005 |
| WO | WO-2007103018 A2 | 9/2007 |
| WO | 2008073187 A2 | 6/2008 |
| WO | 2008104564 A1 | 9/2008 |
| WO | WO-2009007846 A2 | 1/2009 |
| WO | 2009149013 A2 | 12/2009 |
| WO | 2010066252 A1 | 6/2010 |
| WO | WO-2010080287 A1 | 7/2010 |
| WO | WO-2011109769 A1 | 9/2011 |
| WO | 2011130280 A1 | 10/2011 |
| WO | 2011071727 A2 | 12/2011 |
| WO | WO-2012003476 A2 | 1/2012 |
| WO | WO-2012110646 A1 | 8/2012 |
| WO | 2013038306 A1 | 3/2013 |

OTHER PUBLICATIONS

International Searching Authority, Written Opinion, counterpart PCT Application PCT/US2011/027284, mailed Sep. 4, 2012, 6 pages.

International Searching Authority, International Search Report and Written Opinion, PCT Application PCT/EP2012/052800, mailed Jul. 2, 2012, 13 pages.

Zimmerman, K.P. et al., University of Missouri. "On velocity changes caused by tissue fixation," Letters to the Editor in *Ultrasound in Medicine & Biology*, vol. 10, No. 4, Jul.-Aug. 1984. 6 pages.

Bamber, J.C. and C.R. Hill. "Ultrasonic Attenuation and Propagation Speed in Mammalian Tissues as a Function of Temperature." *Ultrasound in Medicine & Biology*, vol. 5, pp. 149-157. Great Britain: Pergamon Press Ltd., 1979.

Bamber, J.C. et al. "Ultrasonic Propagation Through Fixed and Unfixed Tissues." *Ultrasound in Medicine & Biology*, vol. 5, pp. 159-165. Great Britain: Pergamon Press Ltd., 1979.

Hoffmeister, B.K. et al. "Estimation of the elastic stiffness coefficient c13 of fixed tendon and fixed myocardium." *Journal of the Acoustical Society of America* 97(5), May 1995, pp. 3171-3176.

Puchtler, H. and S.N. Meloan. "On the chemistry of formaldehyde fixation and its effects on immunohistochemical reactions." *Histochemistry* (1985) 82:201-204.

Carson, Freida L. "Fixation and Processing" in *Histologic Preparations: Common Problems and Their Solutions*, by Richard W. Brown, Northfield, IL: College of American Pathologists, 2009, pp. 1-5.

Chu, Wei-Sing. "Ultrasound-accelerated Tissue Fixation / Processing Achieves Superior Morphology and Macromolecule Integrity with Storage Stability." *Journal of Histochemistry & Cytochemistry*, vol. 54(5): 503-513, 2006.

Hall, Christopher S. and S.A. Wickline. "High Frequency Ultrasonic Detection of Protein Cross Linking in Myocardial Tissue." 1998 IEEE Proceedings of Ultrasonics Symposium, vol. 2, pp. 1357-1360.

Hall, Christopher S. et al. "High Frequency Ultrasonic Detection of the Temporal Evolution of Protein Cross Linking in Myocardial Tissue." Jul. 2000 IEEE Transactions on Ultrasonics Ferroelectrics & Frequency Control 47(4): 1051-8.

Baldwin, Stephen L. et al. "Ultrasonic Detection of the Anisotropy of Protein Cross-Linking in Myocardium." Sep. 2005 IEEE Ultrasonics Symposium, vol. 4, pp. 2263-2266.

Hill, C.R. et al., editors, Physics Department, Institute of Cancer Research, Royal Marsden Hopspital, Sutton, Surrey, UK. *Physical Principles of Medical Ultrasonics*, second edition. Chichester, England: John Wiley & Sons Ltd., 2004. 511 pages.

Bahr et al. "Volume Changes of Tissues in Physiological Fluids During Fixation in Osmium Tetroxide or Formaldehyde and During Subsequent Treatment," *Experimental Cell Research*, 1957, vol. 12, pp. 342-355.

Boon et al. "Formaldehyde fixation and microwave irradiation," *Histochemical Journal*, 1988, vol. 20, pp. 313-322.

DiDonato et al. "Fixation Methods for the Study of Lipid Droplets by Immunofluorescence Microscopy," *The Journal of Histochemistry & Cytochemistry*, 2003, vol. 51(6), pp. 773-780.

Durgan-Yucei et al. "Rapid fixation of whole organ specimens and attendant problems," *Acta Medica Okayam*, Apr. 1992, vol. 46, Issue 2, Article 3, pp. 75-81.

Fowler, et al. "Modeling formalin fixation and histological processing with ribonuclease A: effects of ethanol dehydration on reversal of formaldehyde cross links," *Laboratory Investigation*, Jul. 2008, vol. 88, pp. 785-791.

Hamberg et al. "A novel method for the detection of porcine circovirus type 2 replicative double stranded viral DNA and nonreplicative single stranded viral DNA in tissue sections," *Journal of Veterinary Diagnostic Investigation*, 2007, vol. 19, pp. 135-141.

Hafajee et al. "Ultra-rapid microwave-stimulated tissue processing with a modified protocol incorporating microwave fixation," *Pathology*, 2004, vol. 36, No. 4, pp. 325-329.

Holt et al. "Studies on Formalin Fixation for Electron Microscopy and Cytochemical Staining Purposes," *The Journal of Biophysical and Biochemical Cytology*, 1961, vol. 11, pp. 31-45.

Hopwood, D. "Microwaves and Heat in Aldehyde Fixation: Model Experiments with Bovine Serum Albumin," *Methods: A Companion to Methods in Enzymology*, 1998, vol. 15, pp. 119-122.

(56) References Cited

OTHER PUBLICATIONS

Ichimura et al. "Formaline fixation by boiling: is it suitable for the TUNEL staining?" *Pathology International*, 1995, vol. 45, No. 12, pp. 971-972.
Iesurum et al. "Microwave Processing and Ethanol-Based Fixation in Forensic Pathology," *The American Journal of Forensic Medicine and Pathology*, Jun. 2006, vol. 27, No. 2, pp. 178-182.
Koshiba et al. "The Effect of Formalin Fixation on DNA and the Extraction of High-molecular-weight DNA from Fixed and Embedded Tissues," *Path. Res. Pract.*, 1993, vol. 189, pp. 66-72.
Lagerstedt, Sten. "The effect of formaldehyde-fixation on the amount of ultraviolet absorbing substances related from tissue sections in the histochemical ribonuclease test," *Z Zellfrosch Mikrosk Anta.*, 1957, vol. 45(4), pp. 472-482.
Lowry et al. "Immunohistochemical methods for semiquantitative analysis of collagen content in human peripheral nerve," *Journal of Anatomy*, 1997, vol. 191, pp. 367-374.
Manger et al. "Acquisition of brains from the African elephant (*Loxodonta africana*): Perfusion-fixation and dissection," *Journal of Neuroscience Methods*, 2009, vol. 179, pp. 16-21.
Manning et al. "Simultaneous Formalin Fixation and EDTA Decalcification, with Carbowax Embedding for Preservation of Acid Phosphatase," *Stain Technology*, 1965, pp. 7-12.
Noguchi et al. "Modified formalin and methanol fixation methods for molecular biological and morphological analyses," *Pathology International*, 1997, vol. 47, pp. 685-691.
Rait et al. "Modeling formalin fixation and antigen retrieval with bovine pancreatic RNase A II. Interrelationship of cross-linking, immunoreactivity, and heat treatment," *Laboratory Investigation*, 2004, vol. 84, pp. 300-306.
Rait et al. "Modeling formalin fixation and antigen retrieval with bovine pancreatic ribonuclease A: I—Structural and functional alterations," *Laboratory Investigation*, 2004, No. 84, pp. 292-299.
Ruijter et al. "Rapid Microwave-Stimulated Fixation of Entire Prostatectomy Specimens," *Journal of Pathology*, 1997, vol. 183, pp. 369-375.
Van Valkenburg et al. "The use of microwave irradiation with low formalin concentrations to enhance the conversion of dopamine into norsasolinol in rat brain: a pilot study," *Histochemical Journal*, 1990, vol. 22, pp. 353-357.
Walker et al. "The Use of Formalin Fixation in the Cytochemical Demonstration of Succinic and DPN- and TPN-Dependent Dehydrogenases in Mitchondria," *The Journal of Cell Biology*, 1963, vol. 16, pp. 455-469.
Zeikus et al. "Use of Hot Formaldehyde Fixative in Processing Plant-Parasitic Nematodes for Electron Microcopy," *Stain Technology*, 1975, vol. 50, No. 4, pp. 219-225.
Holczinger, Von L. "Formation of aldehyde groups in tissues after formal fixation," *Acta Histochemica*, 1958, vol. 6(1-4), pp. 36-43.
Lampton, Michael. "Damping-Undamping Strategies for the Levenberg-Marquardt Nonlinear Least-Squares Method," *Computers in Physics*, vol. 11, No. 1, Jan./Feb. 1997, pp. 110-115.
Chartrand, Rick. "Numerical differentiation of noisy, nonsmooth data," published by Los Alamos National Laboratory, Dec. 13, 2005, pp. 1-9.
Wolff, Antonio C. et al. "American Society of Clinical Oncology/College of American Pathologists Guideline Recommendations for Human Epidermal Growth Factor Receptor 2 Testing in Breast Cancer," *Journal of Clinical Oncology ASCO Special Article*, vol. 25, No. 1, Jan. 1, 2007, pp. 118-145.
Lawson, Alison et al. "Cytotoxicity Effects of Cryoprotectants as Single-Component and Cocktail Vitrification Solutions," Author Manuscript published in *Cryobiology*, Apr. 2011, 18 pages.
Shibutani et al. "Methacarn Fixation: A Novel Tool for Analysis of Gene Expressions in Paraffin-Embedded Tissue Specimens," The United States and Canadian Academy of Pathology, Inc., Laboratory Investigation vol. 80, No. 2, Copyright 2000, pp. 199-208.
Azhari, H., "Typical Acoustic Properties of Tissues," in: Azhari, H., Basics of Biomedical Ultrasound for Engineers, (Wiley—IEEE Press, Mar. 15, 2010), pp. 313-314.
Gueuning et al., "Accurate Distance Measurement by an Autonomous Ultrasonic System Combining Time-of-Flight and Phase-Shift Methods," IEEE Instrumentation and Measurement, Technology Conference, Brussels, Belgium, Jun. 4-6, 1996, pp. 399-404.
Marioli et al., "Digital Time-of-Flight Measurement for Ultrasonic Sensors," IEEE Transactions of Instrumentation and Measurement, vol. 41, No. 1, Feb. 1992, pp. 93-97.
Marutyan et al., "The Frequency Dependence of Ultrasonic Velocity and the Anisotropy of Dispersion in Both Freshly Excised and Formalin-Fixed Myocardium," Ultrasound in Medicine and Biology, vol. 32, No. 4, Apr. 2006, pp. 603-610.
Sarvazyan et al., "Ultrasonic Assessment of Tissue Hydration Status," Ultrasonics, vol. 43, No. 8, Aug. 2008, pp. 661-671.
Svilainis et al., "The time-of-flight estimation accuracy versus digitization parameters," ULTRAGARSAS (Ultrasound), vol. 63, No. 1, 2008 pp. 12-17.
Berod et al., "Importance of Fixation in Immunohistochemistry," The Journal of Histochemistry and Cytochemistry, vol. 29, No. 7, Feb. 7, 1981, pp. 844-850.
Mathews et al., "Shaping policy: the Canadian Cancer Society and the Hormone Receptor Testing Inquiry," Current Oncology, vol. 18, No. 4, Aug. 2008, pp. 174-179.
Plebani et al., "Mistakes in a stat laboratory: types and frequency," Clinical Chemistry, vol. 43, No. 8, Aug. 1997, pp. 1348-1351.
Middleton et al., "Implementation of American Society of Clinical Oncology/College of American Pathologists HER2 Guideline Recommendations in a Tertiary Care Facility Increases HER2 Immunohistochemistry and Fluorescence In Situ Hybridization Concordance and Decreases the Number of Inconclusive Cases," Archives of Pathology Laboratory Medicine, vol. 133, May 2009, pp. 775-780.
Engel et al., "Effects of Preanalytical on the Detection of Proteins by Immunohistochemistry in Formalin-Fixed Paraffin-Embedded Tissue," Archives of Pathology Laboratory Medicine, vol. 135, May 2011, pp. 537-543.
Wolff et al., "American Society of Clinical Oncology/College of American Pathologists Guideline Recommendations for Human Epidermal Growth Factor Receptor 2 Testing in Breast Cancer," Archives of Pathology Laboratory Medicine, vol. 135, Jan. 2007, pp. 18-43.
"Histonet post re phosphoproteins", posted Apr. 16, 2010, https://www.mail-archive.com/search?I=histonet@lists.utsouthwestern.edu&q=subject:%22%5BHistonet%5D+Phospho+antibodies+and+fixation%22&o=newest&f=1, printed Apr. 19, 2016, pp. 1-5.
Chafin et al., Rapid Two-Temperature Formalin Fixation, PLOS ONE, www.plosone.org, e54138, Jan. 18, 2013, vol. 8, Issue 1, pp. 1-16. http://journals.plos.org/plosone/article/asset?id=10.1371%2Fjournal.pone.0054138.PDF.
Meng et al., High level of AKT activity is associated with resistance to MEK inhibitor AZD6244 (ARRY-142886), NIH-PA Author Manuscript from Cancer Biol Ther., Nov. 2009; 8 (21): pp. 2073-2080.
U.S. Appl. No. 61/463,551, filed Feb. 17, 2011.
Facilitated. (n.d.). Dictionary.com Unabridged. Retrieved Feb. 16, 2017 from Dictionary.com website http://www.dictionary.com/browse/facilitated.
Bauer et al, 2014, "Dynamic Subnanosecond Time-of-Flight Detection for Ultra-precise Diffusion Monitoring and Optimization of Biomarker Preservation", Proceedings of SPIE, 9040:90400B1-90400B10.
Bussolati et al, 2011, "Formalin Fixation at Low Temperature Better Preserves Nucleic Acid Integrity", PLoS ONE, 6(6):e21043 (8 pp.).
Carson, Freida L., 2015, "Histotechnology, A Self Instructional Text", Histotechnology 4e, pp. 159-279.
Everett et al, 2011, "Mitotic phosphorylation activates hepatoma-derived growth factor as a mitogen, BMC Cell Biology", 12(15):9 pp.
Krueger et al, 2006, "Posttranslational Protein Modifications: Current Implications for Cancer Detection, Prevention, and Therapeutics, Molecular & Cellular Proteomics", 5(10):1799-1810.
Mueller et al, 2010, "Reverse phase protein microarrays advance to use in clinical trials", Molecular Oncology, 4:461-481.

(56) References Cited

OTHER PUBLICATIONS

Neumeister et al, 2012, "Quantitative Assessment of Effect of Preanalytic Cold Ischemic Time on Protein Expression in Breast Cancer Tissues", JNCI, 104(23):1814-1824.
Oyama et al, 2007, "The Effects of Fixation, Processing and Evaluation Criteria on Immunohistochemical Detection of Hormone Receptors in Breast Cancer", Breast Cancer, 14(2):182-188.
Peracchia et al., New Glutaraldehyde Fixation Procedures, J. Ultrastructure Research, 1972, pp. 57-64, No. 39.

* cited by examiner

FIG. 3C
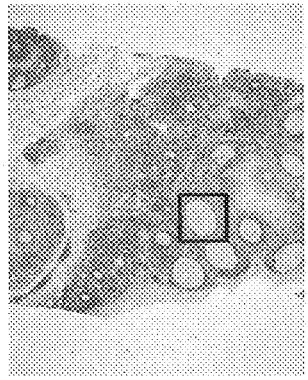
FIG. 3F
FIG. 3H
FIG. 3B
FIG. 3E
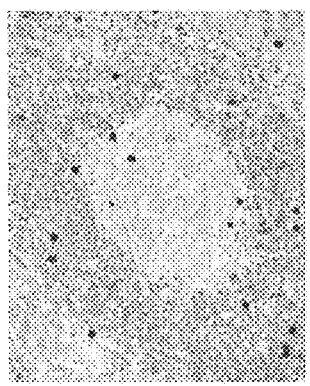
FIG. 3G
FIG. 3A
FIG. 3D
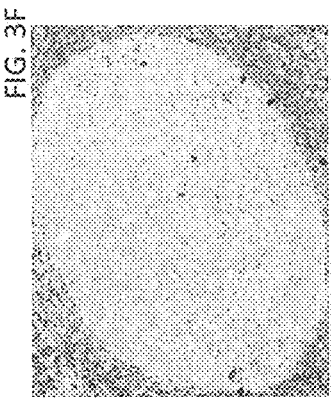

| | Controls | Experimental | | | |
|---|---|---|---|---|---|
| | RT | 35°<br>10% NBF | 40°<br>10% NBF | 45°<br>10% NBF | 50°<br>10% NBF |
| Poor | 0 hr | 0.5 hr | 0.5 hr | 0.5 hr | 0.5 hr |
| | 2 hr | 1 hr | 1 hr | 1 hr | 1 hr |
| Intermeidate | 4 hr | 2 hr | 2 hr | 2 hr | 2 hr |
| | 8 hr | 4 hr | 4 hr | 4 hr | 4 hr |
| Good | 24 hr | 6 hr | 6 hr | 6 hr | 6 hr |

FIG. 6

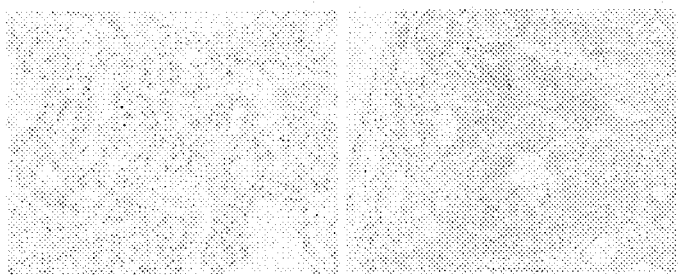
FIG. 11A FIG. 11B FIG. 11C
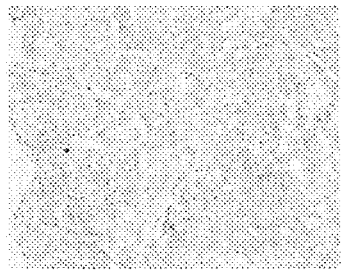
FIG. 11D FIG. 11E
20x Images

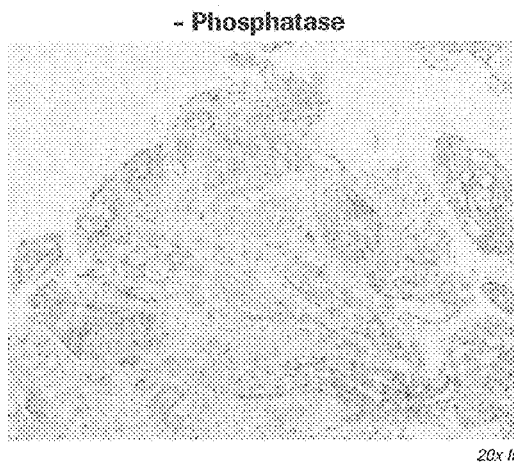
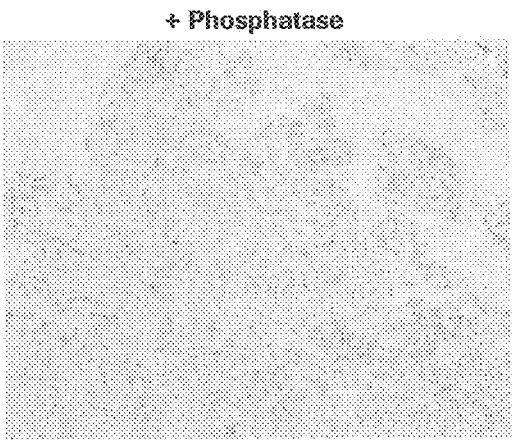
FIG. 12A  FIG. 12B
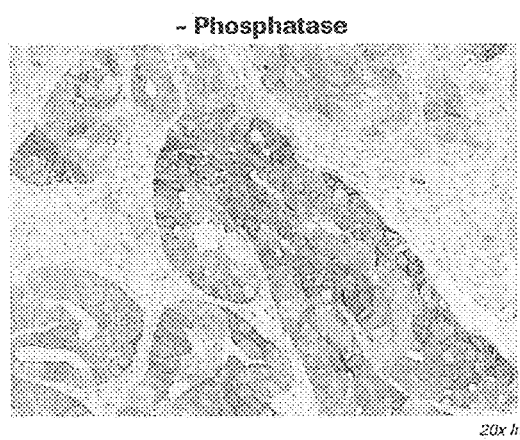
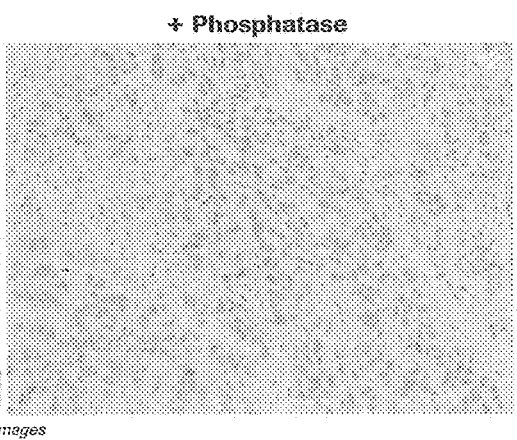
FIG. 12C  FIG. 12D 2x Images

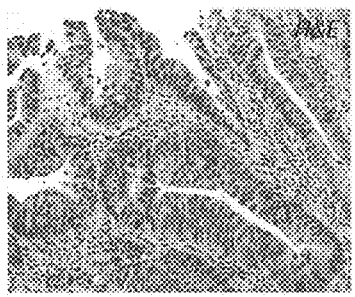
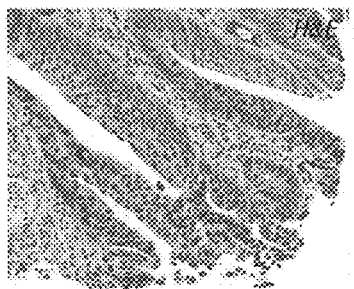
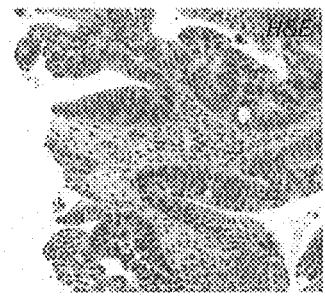
FIG. 16A | FIG 16B | FIG. 16C
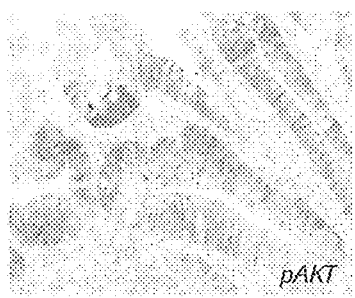
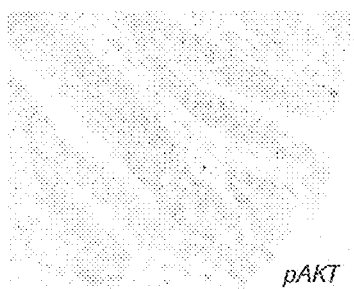
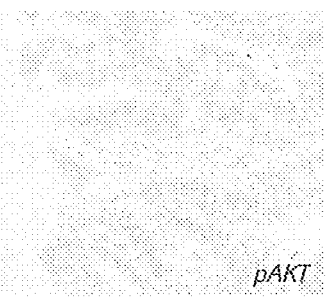
FIG. 16D | FIG. 16E | FIG. 16F
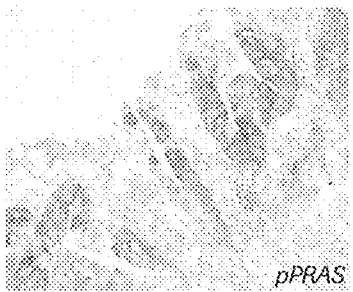
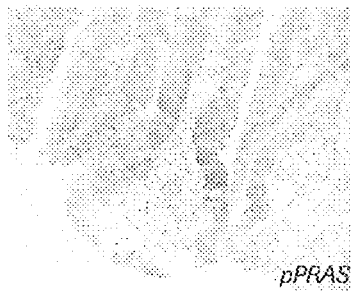
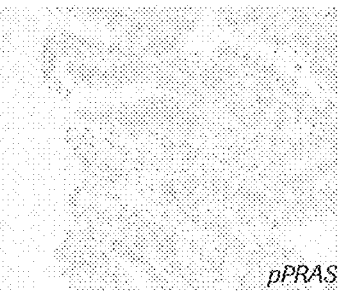
FIG. 16G | FIG. 16H | FIG. 16I

METHOD FOR TISSUE SAMPLE FIXATION

CROSS REFERENCE TO RELATED APPLICATION

The present application is a continuation-in-part under 35 U.S.C. § 120 of international application PCT/US2011/027284, filed on Mar. 4, 2011, which claims the benefit under 35 U.S.C. § 119(e) of U.S. provisional application Ser. No. 61/310,653, filed Mar. 4, 2010; the present application also claims the benefit under 35 U.S.C. § 119(e) of U.S. provisional application Ser. No. 61/464,479, filed on Mar. 4, 2011, and U.S. provisional application Ser. No. 61/463,551, filed on Feb. 17, 2011. International application PCT/US2011/027284 and U.S. provisional application Ser. Nos. 61/464,479 and 61/463,551 are incorporated herein by reference.

FIELD

Disclosed embodiments concern processing tissue samples by aldehyde fixation, such as formalin fixation of tissue samples for subsequent staining and imaging of the sample for pathological interpretation.

BACKGROUND

Formalin has been used by the histology field for over half a century. When used at room temperature, formalin diffuses into a tissue section and cross-links proteins and nucleic acids, thereby halting metabolism, preserving biomolecules and readying the tissue for paraffin wax infiltration. In practice, formalin fixation primarily occurs at room temperature or higher. Some groups perform fixation at slightly elevated temperatures, presumably to increase the cross-linking rate. Just as heat increases cross-linking rate, cold formalin significantly decreases cross-linking rate. For this reason, histologists typically perform tissue fixation at room temperature or higher. Some groups have used cold formaldehyde, but only in specialized situations and not for fixing tissues. For instance, groups use cold formalin to examine lipid droplets or other special situations.

Several effects are observed in tissues that are either under exposed or over exposed to formalin. If a tissue sample is not treated with formalin for a sufficiently long period of time, tissue morphology is typically very poor when the tissues are subjected to standard tissue processing. For example, in inadequately fixed tissue, subsequent exposure to ethanol shrinks the cellular structures and condenses nuclei since the tissues will not have the chance to form a proper cross-linked lattice. When under fixed tissue is stained, such as with hematoxylin and eosin (H&E), many white spaces are observed in between the cells and tissue structures, condensed nuclei and loss of cytoplasm, and samples appear pink and unbalanced with the hematoxylin stain. Tissues that have been exposed to formalin too long typically do not work well for subsequent immunohistochemical processes, presumably because of nucleic acid and/or protein denaturation and degradation. As a result, the optimal antigen retrieval conditions for these tissues do not work properly and therefore the tissue samples appear to be under stained.

Proper medical diagnosis and patient safety require properly fixing the tissue samples prior to staining. Accordingly, guidelines have been established by oncologists and pathologists for proper fixation of tissue samples. For example, according to the American Society of Clinical Oncology (ASCO), the current guideline for fixation time in neutral buffered formalin solution for HER2 immunohistochemistry analysis is at least 6 hours, preferably more, and up to 72 hours. It would be advantageous to develop a process for rapidly fixing tissue samples both to better preserve biological molecules and tissue morphology before significant degradation occurs, and to provide accurate test results to medical professionals and patients as quickly as possible.

Such a process is particularly important for preserving post-translational modification signals. Post-translational modification of proteins plays an extremely important role in cellular metabolism. For instance, phosphorylation of proteins regulates many cellular functions such as cell cycle control, replication, transcription and translation. Other modifications like ubiquitination may target those proteins for degradation and have profound effects on cellular functions. Unfortunately, when the cell loses control of some of these modifications, cellular proliferation results and cancers arise. In fact, most cancer pathways are now being linked integrally with phosphorylation cascades that ultimately cause cells to become immortalized and diagnosed as cancerous. It will be extremely important for researchers and companies to understand if certain modifications exist in cancers as a way of diagnosing a particular cancer type and/or predicting treatment outcome.

Unfortunately, currently existing methods, typically requiring long fixation and processing times at room temperature, are not good for preserving protein modifications. The issue of losing modification signals of proteins has been addressed by many researchers in the past, for example, halting the action of phosphatases for example, Millipore (Kinase Inhibitor Cocktail) Cat #20-116), Thermo Scientific (Halt Phosphatase Inhibitor Cocktail) Cat#78420) etc.

Others in the industry have developed fast freezing methods in order to halt the action of modification enzymes (Lawson et. al. Cytotoxicity effects of cryoprotectants as single-component and cocktail vitrification solutions, 2011, vol. 62, issue 2, pages 115-122). Fast freezing methods generally apply to the instances where whole organs need to be preserved for implantation and involve DMSO or sugars. Unfortunately, fast freezing may initially slow down the action of such enzymes but does not inhibit their action upon thawing of the sample. These approaches all have various limitations.

The above approaches are mainly useful for inhibiting modification enzymes in tissue extracts or cell lines due to the poor diffusion properties or lack of effectiveness of most phosphatase inhibitors in solid tissues. Larger molecular inhibitors such as proteins will have extremely low diffusion rates. Smaller molecules such as orthovanadate have higher diffusion rates but limited specificity and are not extremely effective against all phosphatases. There is not currently available a universal, easy to implement method of halting the action of modification enzymes effectively in solid tissue samples. Thus, it is desirable in the art to develop novel tissue fixing methods offering excellent quality in preserving tissue morphology, protein structure and/or post-translation modification signals.

SUMMARY

The present invention is directed to methods for fixing tissues. In typical embodiments, the methods offers excellent quality in preserving tissue morphology, protein structure and/or post-translation modification signals.

Certain disclosed embodiments concern a method for aldehyde fixation, exemplified by formalin fixation, of a tissue sample, comprising applying, immersing or otherwise contacting an aldehyde solution and a tissue sample for a first time period and at a first temperature, and then raising the temperature of the tissue sample to a second temperature higher than the first temperature for a second time period.

The aldehyde solution and tissue sample are typically in contact with each other at the first temperature for a period of time effective to allow the aldehyde solution to diffuse throughout substantially the entire cross section of the tissue sample.

The tissue sample second temperature is higher than the first temperature. The raising of the tissue sample temperature may comprise raising the temperature of the tissue sample rapidly quickly or even abruptly to the second temperature. The raising of the sample temperature is done to increase cross-linking while still preserving the underlying sample reactivity. Alternatively, the raising of the tissue sample to the second temperature may be accomplished by immersing the tissue sample in a solution at the second temperature, wherein the solution can be the same or a different aldehyde solution. The second temperature typically is greater than ambient, more typically is greater than about 22° C., even more typically is from greater than about 22° C. to at least about 50° C., and even more typically is from greater than about 22° C. to about 45° C. The second time period is effective to allow substantially complete cross-linking of endogenous molecules and structures to occur. While the second time period may vary, it typically ranges from greater than 15 minutes up to at least about 5 hours, typically is from about 1 hour to about 4 hours, and even more typically is from about 2 hours to about 3 hours. The speed and methods used for raising the temperatures are so designed that optimal preservation of post-translation modification signals is achieved.

While the first time period may vary depending on tissue thickness, for ASCO CAP guidelines of up to 4 mm thickness, it typically ranges from about 15 minutes up to about 4 hours, more typically from greater than 15 minutes to about 3 hours, and even more typically is from about 1 hour to about 2 hours. It is recognized that for thicker samples, the first time period will be dictated by diffusion rate. The first temperature is from at least −20° C. to about 15° C., typically is from at least 0° C. to about 15° C., more typically at least 0° C. to about 10° C., and even more typically from about 3° C. to about 5° C.

Certain embodiments of the method comprise applying a first aldehyde solution at a first temperature to the tissue sample, followed by applying a second aldehyde solution to the tissue sample. The second aldehyde solution may be different from the first aldehyde solution. For example, the solutions can be at different concentrations, or the second aldehyde solution may comprise an aldehyde different from the first aldehyde. The aldehyde typically is a lower alkyl aldehyde, such as formaldehyde, glutaraldehyde, or combinations thereof.

One disclosed exemplary embodiment of the present invention comprises immersing a tissue sample into a formalin solution at a temperature of from equal to or greater than 0° C. up to no greater than 5° C. for a first period of from greater than 15 minutes up to about 4 hours. The tissue sample is then immersed into a formalin solution at a second temperature greater than about 22° C. up to at least 45° C. for a second time period of from about 1 hour to about 4 hours. The formalin solution generally is 10% NBF. These processing steps typically are followed by a series of alcohol washes, further followed by a clearing solution wash, such as a xylene wash, of from greater than 0 minutes up to at least about 30 minutes, or to about 1, about 2, about 3, or about 4 hours. Wax is then applied to the tissue sample to form a wax impregnated block.

As currently understood, no one to date has used a cooled and heated fixative approach to increase the quality of tissue fixation. Without being bound by a theory of operation, it currently is believed that at reduced temperature, very little cross-linking occurs but fixative solution does penetrate into substantially the whole tissue section. Additionally, it may be that metabolic or enzymatic processes are dramatically reduced. Once diffused, the temperature is rapidly raised, where cross-linking kinetics are greatly increased. Using this process, in some embodiments, high quality tissue morphology and IHC staining known in the art, has been accomplished in approximately 4 hours compared to 24 hours for room temperature protocols. In addition, since fixative solution has substantially diffused into the sample, more even morphologic and antigen preservation are observed. This protocol differs from the prior art by separating the fixation process into a first process step that permits diffusion of fixative solution into a tissue sample but minimizes cross-linking, and a second process step that increases the rate of cross-linking, during the time periods typically used for fixing a tissue sample in disclosed working embodiments.

In typical embodiments, the methods preserve post-translation modification signals of proteins in the tissue sample significantly, for example, by preserving at least 30%, 50%, 70%, or 90% post-translation modification signals. The tissue fixation methods of the present invention can significantly halt the enzyme activities destroying the post-translation modification signals, such as halting the enzyme activities of phosphatase.

In another typical embodiment, the methods preserve signals of proteins in the tissue sample significantly, for example, by preserving at least 30%, 50%, 70%, or 90% post-translation modification signals. The tissue fixation methods of the present invention can significantly halt the enzyme activities degrading proteins, such as halting the enzyme activities of protease.

In one exemplary embodiment, formaldehyde fixed-paraffin embedded (FFPE) tissue samples are used. The present method offers several advantages over existing attempts to preserve modification states from FFPE tissue. The method uses a standard formalin solution that is in wide use in histology practice. The cold step can be carried out in a simple manner consisting of cold formalin followed by heated formalin. The present invention for the first time in the art accomplishes preserving modification states in FFPE tissue. The present technique is more rapid than existing fixation methods and can significantly reduce the turn-around time for tissue specimens and improve information flow.

In summary, the present method offers at least three improvements over existing methods in the art. First, by allowing formalin to penetrate into the tissue section in a cold environment can significantly reduce enzyme activities. Second, by increasing the cross-linking kinetics by quickly raising the tissue sample temperature, the cellular constituents are "locked" into place more rapidly than what would be observed at room temperature. This combination makes this technique superior over existing methods and for the first time allows modification states to be preserved in FFPE tissues. Third, this represents a general method believed to be applicable to a wide variety of modification states and enzymes. While other methods target a specific set of modification enzymes, this method rapidly disables all modification enzymes and therefore preserve the general cellular status much better than gold standard room temperature procedures. Since the invention is not limited to a specific set of biomolecules or biomolecules containing specific post-translations modifications, it is believed that this method represents a general method for preservation of any biomolecule or modification state. Thus, this invention can preserve with high quality quantities of biomolecules and biomolecules containing specific post-translations modifications.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3H are digital microscope images of tissue samples treated according to different processing protocols illustrating that pre-soaking tissue samples for 10 minutes, 30 minutes and 60 minutes (A-C, and D-F, respectively) with 10% neutralized buffered formalin solution increases staining quality when tissue samples are treated with bcl-2, diaminobenzidine and a hematoxylin reagent; FIGS. 3A-3C are images obtained with no pre-soaking and a 40° C. treatment with 10% neutralized buffered formalin solution; FIGS. 3D-3F are samples treated with a 4° C., 2 hour pre-soak in 10% neutralized buffered formalin solution followed by a 40° C. fixation with 10% neutralized buffered formalin solution; and FIGS. 3G and 3H are blowups of the regions indicated in FIGS. 3C and 3F, respectively.

FIG. 6 is a graphical representation of antigenicity results obtained by bcl-2 immunohistochemistry analysis using tissue samples treated for different time periods of 0.5-6 hours with 10% neutralized buffered formalin solution at 35° C., 40° C., 45° C., and 50° C.

FIGS. 11A-E are microscopic images of staining for pAKT on Calu-3 xenografts.

FIGS. 12A-D are microscopic images of staining for pAKT on Calu-3 xenografts with or without phosphate treatment.

DETAILED DESCRIPTION

I. Abbreviations, Terms and Introduction

Figure 1A:
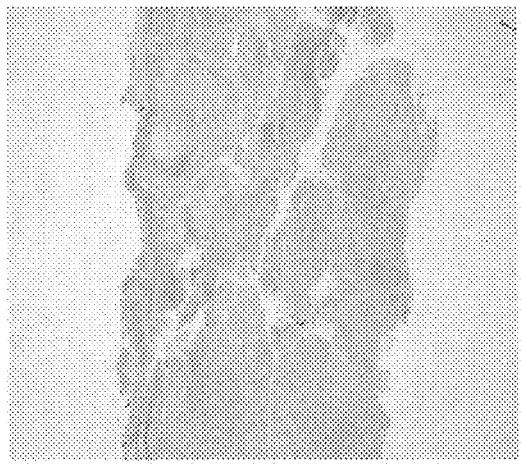
FIGS. 1A-1D are digital microscope images of tissue samples treated for different time periods (0, 2, 4 and 24 hours, respectively) with Cyclin D1, illustrating the effect that fixation state has on the intensity of staining results obtained using antibodies.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" is used in its legally accepted definition and manner, and nothing herein is intended to change such meaning. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of abbreviations and specific terms are provided:

H&E: Hematoxylin and eosin staining.

IHC: Immunohistochemistry.

ISH: In situ hybridization.

NBF: neutralized buffered formalin solution.

Aldehydes: For the purpose of the present invention, the term "aldehydes" refers to a cross-linking type of fixatives containing aldehydes. Many examples of cross-linking fixatives, containing aldehydes are commonplace in histology, including Bouin's, Glyoxal, Zinc-formalin, Acidic-formalin (AFA) and gluteraldehyde.

Alkyl: A saturated aliphatic chain.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antigen: A compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens. In one example, an antigen is a *Bacillus* antigen, such as γPGA.

Epitope: An antigenic determinant. These are particular chemical groups or contiguous or non-contiguous peptide sequences on a molecule that are antigenic, that is, that elicit a specific immune response. An antibody binds a particular antigenic epitope.

Formalin: Commercial solutions of formaldehyde in water commonly used for preservation of biological specimens. Formalin used as a fixative typically is 10% neutral buffered formalin (NBF), but other solution concentrations also can be used. Thus, useful formalin fixation concentrations typically range from greater than 0% up to at least 20%, more typically from 5% up to 15%, with certain disclosed working embodiments of the present invention using a 10% NBF solution to fix tissue samples.

Hapten: A molecule, typically a small molecule that can combine specifically with an antibody, but typically is substantially incapable of being immunogenic except in combination with a carrier molecule.

Immune Response: A response of a cell of the immune system, such as a B-cell, T-cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Lower alkyl: A saturated aliphatic chain that contains 1-10 carbon atoms.

Mammal: This term includes both human and non-human mammals. Similarly, the term "subject" includes both human and veterinary subjects.

Molecule of interest or Target: A molecule for which the presence, location and/or concentration is to be determined. Examples of molecules of interest include proteins and nucleic acid sequences.

Monoclonal antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

Multiplex, -ed, -ing: Detecting multiple targets in a sample substantially simultaneously, or sequentially, as desired. Multiplexing can include identifying and/or quantifying nucleic acids generally, DNA, RNA, peptides, proteins, both individually and in any and all combinations.

Neoplasia and Tumor: The process of abnormal and uncontrolled growth of cells. Neoplasia is one example of a proliferative disorder. The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant" Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Protein: A molecule, particularly a polypeptide, comprised of amino acids.

Post-translation modification: The chemical modification of a protein after its translation. It is one of the later steps in protein biosynthesis, and thus gene expression, for many proteins. The posttranslational modification of amino acids extends the range of functions of the protein by attaching it to other biochemical functional groups (such as acetate, phosphate, various lipids and carbohydrates), changing the chemical nature of an amino acid (e.g. citrullination), or making structural changes (e.g. formation of disulfide bridges). Also, enzymes may remove amino acids from the amino end of the protein, or cut the peptide chain in the middle. For instance, the peptide hormone insulin is cut twice after disulfide bonds are formed, and a pro-peptide is removed from the middle of the chain; the resulting protein consists of two polypeptide chains connected by disulfide bonds. Also, most nascent polypeptides start with the amino acid methionine because the "start" codon on mRNA also codes for this amino acid. This amino acid is usually taken off during post-translational modification.

Other modifications, like phosphorylation, are part of common mechanisms for controlling the behavior of a protein, for instance activating or inactivating an enzyme.

Preservation of the post-translational modification signals can be achieved by using the methods disclosed herein. The methods preserve post-translation modification signals of proteins in tissue samples significantly, for example, by preserving at least 50%, 70%, 90% or 99% of post-translation modification signals. In an exemplary embodiment, the immunohistochemical signal of pAKT by the post-translational modification signals is used as an indicator showing preservation the post-translational modification signals.

Proteases: also known as proteolytic enzymes proteinases or, are a large group of enzymes. Proteases belong to the class of enzymes known as hydrolases, which catalyse the reaction of hydrolysis of various bonds with the participation of a water molecule.

Proteases are involved in digesting long protein chains into short fragments, splitting the peptide bonds that link amino acid residues. Some of them can detach the terminal amino acids from the protein chain (exopeptidases, such as aminopeptidases, carboxypeptidase A); the others attack internal peptide bonds of a protein (endopeptidases, such as trypsin, chymotrypsin, pepsin, papain, elastase).

Proteases are divided into four major groups according to the character of their catalytic active site and conditions of action: serine proteinases, cysteine (thiol) proteinases, aspartic proteinases, and metalloproteinases. Attachment of a protease to a certain group depends on the structure of catalytic site and the amino acid (as one of the constituents) essential for its activity.

Sample: A biological specimen containing genomic DNA, RNA (including mRNA), protein, or combinations thereof, obtained from a subject. Examples include, but are not limited to, peripheral blood, urine, saliva, tissue biopsy, surgical specimen, amniocentesis samples and autopsy material. In one example, a sample includes a biopsy of an adenocarcinoma, a sample of noncancerous tissue, and a sample of normal tissue (from a subject not afflicted with a known disease or disorder).

Specific binding moiety: A member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4$ $M^{-1}$ greater or $10^5$ $M^{-1}$ greater than a binding constant for either of the two members of the binding pair with other molecules in a biological sample). Particular examples of specific binding moieties include specific binding proteins (for example, antibodies, lectins, avidins such as streptavidins, and protein A), nucleic acids sequences, and protein-nucleic acids. Specific binding moieties can also include the molecules (or portions thereof) that are specifically bound by such specific binding proteins.

II. Introduction

Fixation preserves a biological sample (tissue or cells) for subsequent examination. There are three main methods for fixing a tissue sample. Heat fixation involves exposing a sample to sufficient heat for sufficient time to abolish the activity of cellular proteins and thereby halt cellular metabolism. Heat fixation generally preserves cellular morphology but not protein structures.

Perfusion fixes a sample by blood flow. A fixative is injected into the heart and spreads through the entire body. This process preserves morphology, but the subject dies and the process is expensive because of the volume of fixative needed.

Chemical fixation involves immersing a tissue sample in a volume of chemical fixative, typically at least 20 times the volume of the tissue to be fixed. The fixative diffuses through the tissue sample and preserves structures (both chemically and structurally) as close to that of living tissue as possible. Cross-linking fixatives, typically aldehydes, create covalent chemical bonds between endogenous biological molecules, such as proteins and nucleic acids, present in the tissue sample. Formaldehyde is the most commonly used fixative in histology. Formaldehyde may be used in various concentrations for fixation, but it primarily is used as 10% neutral buffered formalin (NBF), which is about 3.7% formaldehyde in an aqueous phosphate buffered saline solution. Paraformaldehyde is a polymerized form of formaldehyde, which depolymerizes to provide formalin when heated. Glutaraldehyde operates in similar manner as formaldehyde, but is a larger molecule having a slower rate of diffusion across membranes. Glutaraldehyde fixation provides a more rigid or tightly linked fixed product, causes rapid and irreversible changes, fixes quickly and well at 4° C., provides good overall cytoplasmic and nuclear detail, but is not ideal for immunohistochemistry staining. Some fixation protocols use a combination of formaldehyde and glutaraldehyde.

III. Development Background

It is well known that tissue fixation kinetics can be increased by raising the temperature of the formalin. However, initial studies conducted by the inventors indicated that placing a tissue sample directly into heated formalin fixative caused the outside of the tissue to cross-link well before formalin penetrated to the center of the tissue. Formalin diffused into dense tissue slower than the cross-linking kinetics at elevated temperatures. In this case, biomolecules in the center are heated without any significant cross-linking, and these molecules therefore are more susceptible to degradation and damage.

Accordingly, some disclosed embodiments of the present invention separate fixative diffusion from unwanted cross-linking by first pre-soaking tissue samples in cold fixative, such as formalin. Then, after the fixative has penetrated the tissue, the fixative temperature can be increased to increase the cross-linking kinetics. This appears to produce a more evenly fixed sample that preserves biomolecules. A series of tissue sample fixation experiments have been conducted using heated formalin only or samples first "pre-soaked" at cold temperature, for example, from −20° C. to 10° C., from −10° C. to 5° C., from −0° C. to 5° C., or 4° C. in formalin, followed by subjecting the same sample to heated formalin.

As a part of this invention, lower temperature solutions that can effectively allow diffusion of fixative into the tissue of interest could possibly be more effective at preserving post translational modifications. Any addition to formalin that reduced the freezing point and thereby allows the fixative to be used at lower than 0° C. could be considered. For example, addition of high concentrations of salts typically reduces the freezing point by several degrees. One could envision addition of salts directly to the formalin solution, thereby keeping the concentration of formaldehyde relatively unchanged. In addition, solutions comprised of glycols or anti-freeze type solutions would also be effective. These solutions might drop the freezing point to as low as −20° C. Examples of different types of chemical additives are known in the art, including, but not limited to, various salts and glycols.

Pre-soaked samples appear to provide superior tissue morphology at the center of the samples as well as better antigen preservation.

IV. Process Steps

Certain disclosed embodiments of the present invention concern a multi-step, typically a two-step, tissue fixation process for infusing/diffusing a tissue sample with an aldehyde fixative, such a formalin and/or glutaraldehyde. During a first step, a tissue sample is treated with a fixative solution under conditions that allow the fixative to diffuse throughout substantially the entire cross section of the sample. This first step is conducted using a fixative composition for a first period of time, and at a first temperature, that effects substantially complete tissue infusion/diffusion. The second step is to subject the tissue sample to fixative composition at a second, higher temperature to allow cross-linking to occur at as fast a rate as possible without compromising the tissue characteristics, such as antigenicity and morphology. Each of these processing steps is discussed in more detail below.

The tissue preparation process initially involves fixative solution diffusion throughout the sample. This typically is accomplished by immersing the tissue sample into a desired fixative composition at a first desired temperature. Some time period after this initial step the tissue sample is removed from the fixative solution at the first temperature and is immersed into a fixative solution at a second temperature higher than the first temperature. This second step is conducted for a second desired time period. The first and second fixative solutions can be the same fixative solution, for example NBF, or different fixative solution. As yet another example, entirely different aldehyde fixatives, such as formaldehyde and glutaraldehyde, might be used for the different steps. And, instead of removing the sample from the fixative solution at the first temperature, the temperature of the fixative can be rapidly increased to a second temperature, such as by using microwave heating. One or both of these steps can be accompanied by mechanical agitation of the fixative solution and/or can be accompanied by application of ultrasound to the sample.

In an exemplary embodiment, the invention described herein uses formalin as the fixative of choice but such is not necessarily required. Formalin contains 3.7% formaldehyde in a phosphate buffer and neutralized to around pH 7.0. However, many variations of cross-linking fixatives, containing aldehydes known in the art of histology can be used in the present invention, including, but not limited to, Bouin's, Glyoxal, Zinc-formalin, Acidic-formalin (AFA) and gluteraldehyde, etc.

The tissue sample is then subjected to a series of alcohol immersions, typically using increasing alcohol concentrations ranging from about 70% to about 100%, to dehydrate the sample. The alcohol generally is an alkanol, particularly methanol and/or ethanol. Particular working embodiments of the present invention have used 70%, 95% and 100% ethanol for these serial dehydration steps.

After the last alcohol treatment step the sample is then immersed into another organic solvent, commonly referred to as a clearing solution. The clearing solution (1) removes residual alcohol, and (2) renders the sample more hydrophobic for a subsequent waxing step. The clearing solvent typically is an aromatic organic solvent, such as xylene. Wax blocks are formed by applying a wax, typically a paraffin wax, to the sample. Slides are then cut from the wax block.

For the following discussion of processing steps, a person of ordinary skill in the art will appreciate that various factors may be considered to deduce optimal processing conditions for a particular tissue sample. These factors include: sample thickness, which typically ranges from about 1 mm to about 10 mm thick, more typically from about 2 mm to about 8 mm thick, and even more typically from about 4 mm to about 6 mm thick; volume of fixative solution to tissue sample mass, which typically is from about 10:1 to about 50:1 volume to mass; fixative composition; temperature; and sample immersion time in the fixative composition.

The preferred description of the first and second times of soaking in cross-linking fixative is based on the ASCO CAP guidelines where the preferred tissue thickness is up to approximately 4 mm. The tissue thickness can be less or more than 4 mm, even up to whole organs. Since the invention relies on a first diffusion step, thicker tissue sections would require a first time in cold fixative greater than the preferred 1-5 hours and up to 12 hours or more. In addition, anyone skilled in the art could understand that the second time in fixative solution might be greater than the preferred method of 1-5 hours and up to 8 hours or more. For example, a tissue sample of 6 mm thick might have a preferred first time in fixative solution of 4 hours and a second time in fixative solution of 4 hours or more. It is also understood in the art that some tissue types and some tissue organs may have slightly different times than the preferred method of the invention.

A. Fixative Diffusion Processing

The first step of the process is to subject a tissue sample to fixative composition under conditions effective to allow substantially complete diffusion of the composition throughout substantially the entire cross section of the sample. An effective temperature range for the first step is from greater than −20° C. to at least 15° C., preferably greater than 0° C. to an upper temperature more typically about 10° C., and even more typically from about 3° C. to about 5° C. For working embodiments, the temperature typically was about 4° C.

As the temperature increases, the rate of cross-linking increases. And this first processing step attempts to balance the beneficial properties associated with substantially complete diffusion of fixative composition throughout the entire cross section of the tissue sample while minimizing the effects associated with initializing cross-linking. However, diffusion also increases with increasing temperature, and so for a given sample, it has been found that maximizing the rate of diffusion while minimizing any deleterious effects associated with increased cross-linking rate appears to increase benefits.

Diffusion of the fixative composition into the tissue sample is continued for a time period effective for diffusion of the composition throughout substantially the entire cross section of the sample. The time period for the first processing step ranges from about 15 minutes up to about 4 hours, most typically from greater than 15 minutes to about 3 hours, with good results typically being obtained by conducting the fixative composition diffusion step for about 1.5 hours to about 2 hours. Increasing the diffusion time to 4 hours or greater generally had little beneficial effect.

The temperature associated with the second processing step typically is higher than ambient, such as higher than about 22° C. For working embodiments, the temperature typically was greater than ambient up to at least 55° C., more typically from about 35° C. to about 45° C., as this temperature range increases the cross-linking kinetics sufficiently to allow relatively quick tissue cross-linking. However, if the temperature is increased above about 50° C., the sample generally begins to degrade, which may have a deleterious effect on certain subsequent histological reactions. Thus, the upper temperature and time period are selected to allow subsequent imaging process steps, such as in situ hybridization, IHC and/or H & E, to proceed effectively. The time period for the second processing step ranges from greater than 15 minutes up to at least about 5 hours, more typically is at least about 1 hour to about 4 hours, and more typically is from about 2 hours to about 3 hours. Certain disclosed working embodiments have conducted the second processing step for 1.5 hours at 45° C.

B. Discussion of Drawings

Figure 1B:
Figure 1C:
Figure 1D:
Figure 2A:
FIGS. 2A-2D are digital microscope images of tissue samples treated for different time periods (0, 2, 4 and 24 hours, respectively) with bcl-2, illustrating the effect that fixation state has on the intensity of staining results obtained using antibodies.
Figure 2B:
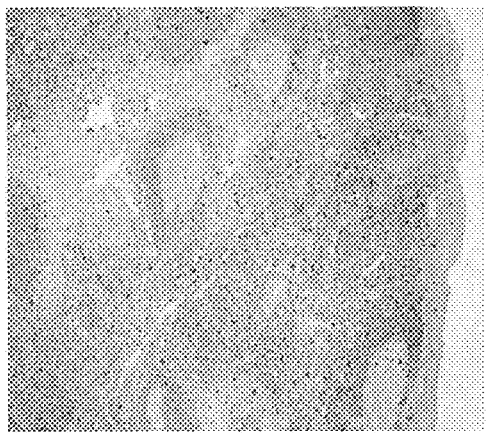
Figure 2C:
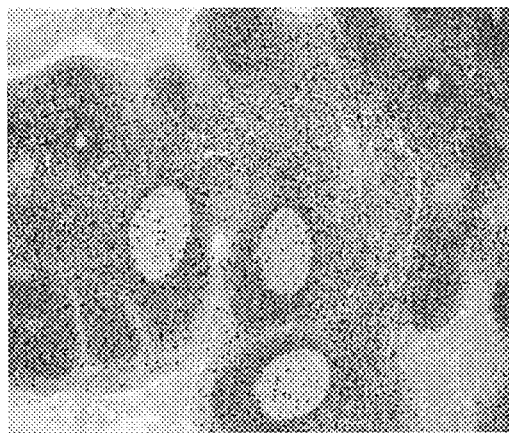
Figure 2D:
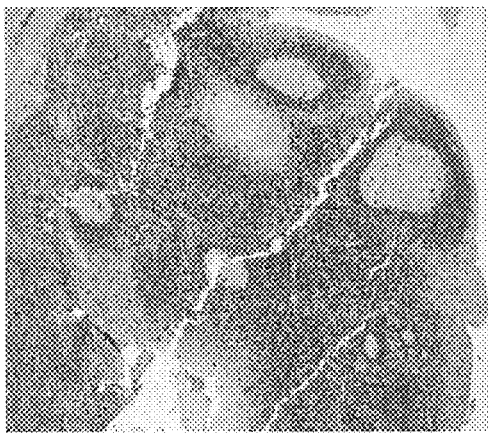

FIGS. 1A-1D (Cyclin D1) and 2A-2D (bcl-2) are from a series of control slides where tissue samples were immersed in room temperature formalin for 0, 2, 4 and 24 hours, respectively. The industry standard requires at least 6 hours, and more typically at least 8 hours, up to 72 hours fixing time in room temperature formalin. The control images provided by FIGS. 1A-1C illustrate that under fixing the tissue sample, i.e. the 0, 2 and 4 hour, processing times, do not stain well using Cylin D1 immunohistochemistry staining protocols. Control slides 2A-2C illustrate that under fixing the tissue sample, i.e. the 0, 2 and 4 hour, processing times, do not stain well using bcl-2 immunohistochemistry staining protocols. However, as would be expected based on known standards, increasing the fixing time to 24 hours, FIGS. 1D and 2D, provides acceptably stained tissue samples.

FIGS. 3A-3H illustrates the effects of using pre-soak processing for bcl-2 staining. FIGS. 3A-3C are images of tissues samples processed with no pre-soak and immersed into a 40° C. 10% NBF solution for 10 minutes, 20 minutes and 60 minutes, respectively. FIGS. 3D-3F are images of tissues samples processed with a 2 hour pre-soak in 10% formalin fixation solution at 4° C., followed by immersion into a 40° C. 10% NBF solution for 10 minutes, 20 minutes and 60 minutes, respectively. FIG. 3G is a blow up of a region from FIG. 3C, and FIG. 3H is a blow up from a region of FIG. 3F. FIG. 3A illustrates an under stained result from no pre-soaking and a 10 minute, 40° C. 10% NBF solution processing. The degree of staining increases with increased processing time for the 30 minute and 60 minute results provided by FIGS. 3B and 3C, respectively. FIGS. 3D-3F also illustrate that pre-soaking provides enhanced staining results. However, perhaps of even more importance is the evenness of the tissue staining that results by applying the different processing protocols. FIGS. 3A-3C are unevenly stained from the outer portion to the inner portion of the sample relative to their time counterparts that were subjected to a 2 hour pre-soak in 10% formalin fixation solution at 4° C. Moreover, each of the pre-soaked samples also had enhanced staining as well.

FIGS. 3G and 3H are from representative areas of FIGS. 3C and 3F, respectively, of germinal centers of a human tonsil sample. FIG. 3C shows that the tissue sample is not as well stained as the representative area of FIG. 3F that was subjected to a 2 hour pre-soak in 10% formalin fixation solution at 4° C. FIG. 3G scored a 2+, and 3H scored a 3+. And, FIG. 3H includes immature lymphocytes in the middle of the slide that have been stained, providing a clear indication that the sensitivity of the staining protocol is substantially increased using the 2 hour pre-soak in 10% formalin fixation solution at 4° C. FIG. 3G does not allow visualization of these lymphocytes.

Figure 4A:
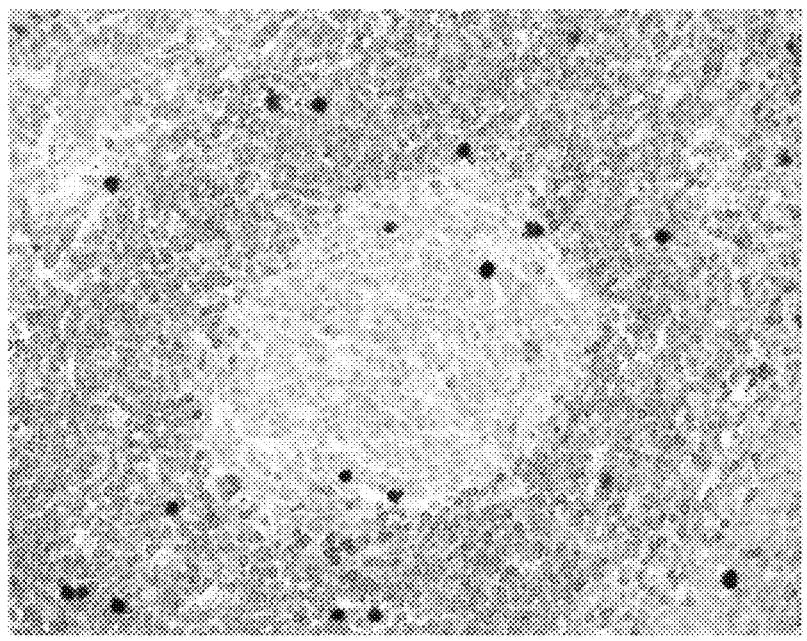
FIGS. 4A-4B are further enlarged digital microscope images of the regions indicated in FIGS. 3C and 3F.
Figure 4B:
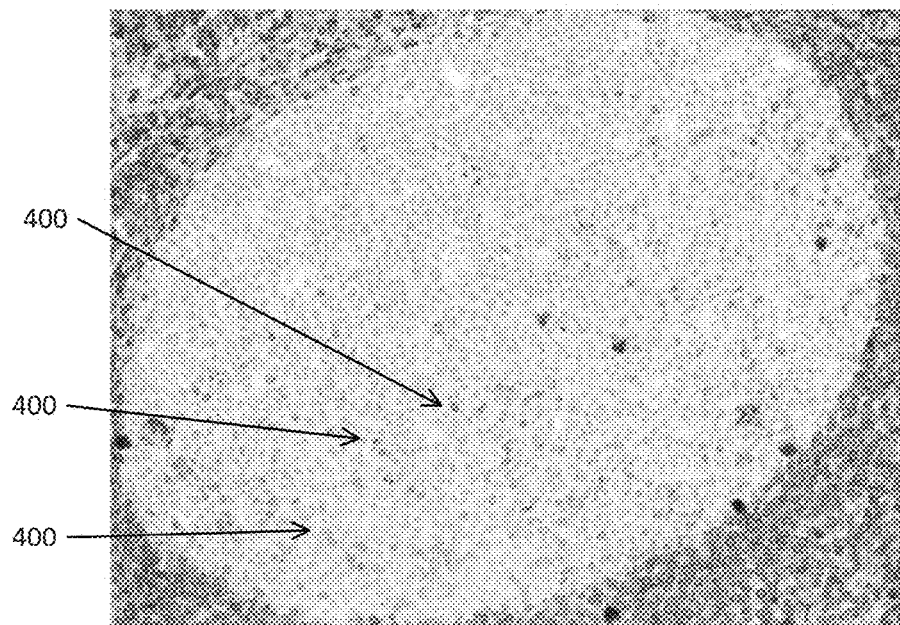

FIGS. 4A and 4B are enhanced images of FIGS. 3G and 3H. The arrows 400 of FIG. 4B illustrate the enhanced detail that results for images produced using a 2 hour pre-soak in 10% formalin fixation solution at 4° C. for these exemplary embodiments. The tissue morphology also is better for the tissue samples produced using a 2 hour pre-soak in 10% formalin fixation solution at 4° C. This can be seen by viewing the left slide of the images and the interior of the images. For tissue samples that were not subjected to a 2 hour pre-soak in 10% formalin fixation solution at 4° C., formalin has not diffused into the interior, and so the morphology of the sample (FIG. 4A) is not as preserved as is the morphology of the tissue sample (FIG. 4B) produced using a 2 hour pre-soak in 10% formalin fixation solution at 4° C. If diffusion is allowed to occur before a later applied increased temperature processing step, the chemicals and structure of the sample are much better preserved. White space in an image illustrates regions that are poorly fixed. When such a tissue sample is later dehydrated, the tissue shrinks and produces a greater volume of white area, which is indicative of poor fixation.

Figure 5:
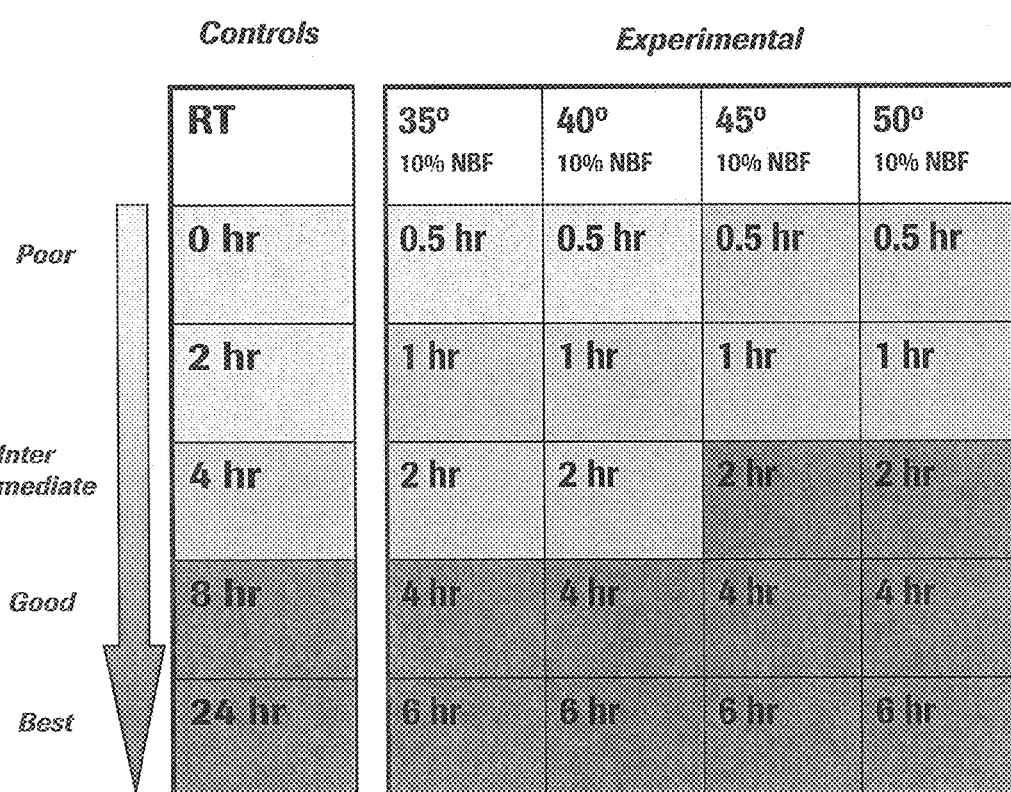
FIG. 5 is a graphical representation of tissue morphology results obtained by treating tissue samples for different time periods of 0.5-6 hours with 10% neutralized buffered formalin solution at 35° C., 40° C., 45° C., and 50° C.

FIG. 5 is a graphical representation of tissue morphology results obtained by H&E staining of tissue samples treated first with a 2 hour pre-soak in 10% formalin fixation solution at 4° C., followed by different time periods of from 0.5 to 6 hours with 10% neutralized buffered formalin solution at 35° C., 40° C., 45° C., and 50° C. relative to room temperature controls. The 24-hour room temperature slide is the desired standard to which processing protocols are compared. FIG. 5 summarizes the results of several trials that focused on determining a best second higher temperature soak that provided superior tissue morphology. While FIG. 5 illustrates the results obtained using a cross-linking processing temperature up to 50° C., much higher processing temperatures also have been tried. Each tissue sample was then subjectively evaluated. A red cell indicates an undesirable result; a yellow cell indicates an intermediate, but not best, result; and a green cell indicates that the tissue sample was comparable to the 24 hour, room temperature result. The higher the temperature, the less time is required to achieve desirable tissue morphology. A person of ordinary skill in the art will appreciate that good tissue samples are provided by treatments of only 2 to 6 hours with a formalin cross-linking processing temperature up to 50° C.

FIG. 6 is graphical representation of bcl-2 immunohistochemistry results obtained using diaminobenzidine staining of tissue samples treated first with 2 hour pre-soak in 10% formalin fixation solution at 4° C., followed by different time periods of from 0.5 to 6 hours with 10% neutralized buffered formalin solution at 35° C., 40° C., 45° C., and 50° C. relative to room temperature controls. Again, the green cells for increased temperature results are results comparable to the 24-hour, room temperature results. For tissue morphology and H&E staining, temperatures and times for the increased temperature processing step do not matter as much, until a temperature of up to 65° C. is used. After that temperature, tissue morphology is deleteriously affected. However, as indicate in FIG. 6, IHC staining is more sensitive to the temperature selected for the upper temperature processing step. Without being limited to a particular theory of operation, it may be that the higher temperatures denature proteins, antibodies do not recognize the epitope on the protein as well or are at all, and therefore degraded IHC staining results. Thus, a particular protocol may best be selected by considering the effects on tissue morphology, IHC and in situ hybridization techniques.

Figure 7:
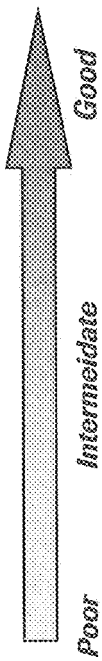
FIG. 7 is a graphical representation of antigenicity results obtained by bcl-2 immunohistochemistry analysis using tissue samples treated with and without pre-soaking and treated for different time periods of 0.5-6 hours with 10% neutralized buffered formalin solution at 35° C., 40° C., 45° C., and 50° C.

FIG. 7 illustrate antigenicity results from IHC staining for no pre-soak test compared to a 2 hour pre-soak in 10% formalin fixation solution at 4° C. Heating is generally potentially harmful to a tissue sample. This can be seen for the no pre-soak test results. Any heating at 45° C. and 50° C. of a sample not subjected to a 2 hour pre-soak in 10% formalin fixation solution at 4° C. had a strong negative impact on the antigenicity staining results. In contrast, for samples that were subjected to a 2 hour pre-soak in 10% formalin fixation solution at 4° C., heating the tissue sample at 45° C. and 50° C. for as little as 0.5 hour up to 1 to 2 hours produced an image result that was comparable to a 24-hour room temperature process.

Figure 8:
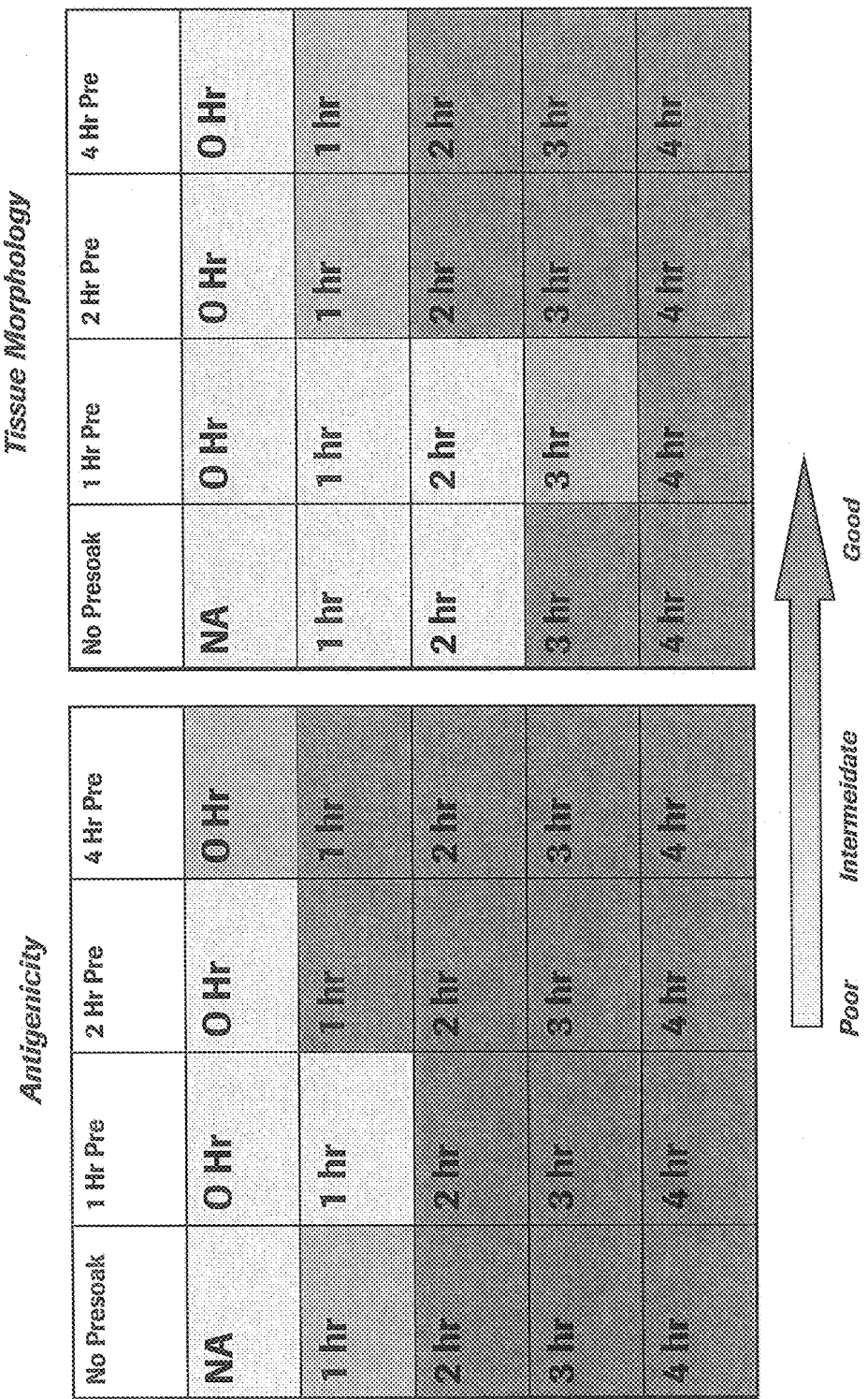
FIG. 8 is a graphical representation of antigenicity and tissue morphology results of tissue samples processed with varying pre-soak times compared to no pre-soak controls.
Figure 9:
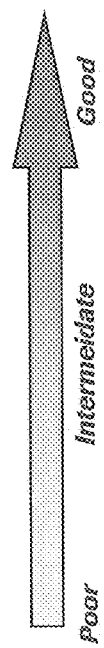
FIG. 9 is a graphical representation of antigenicity and tissue morphology results of tissue samples processed with varying pre-soak times compared to no pre-soak controls.
Figure 10:
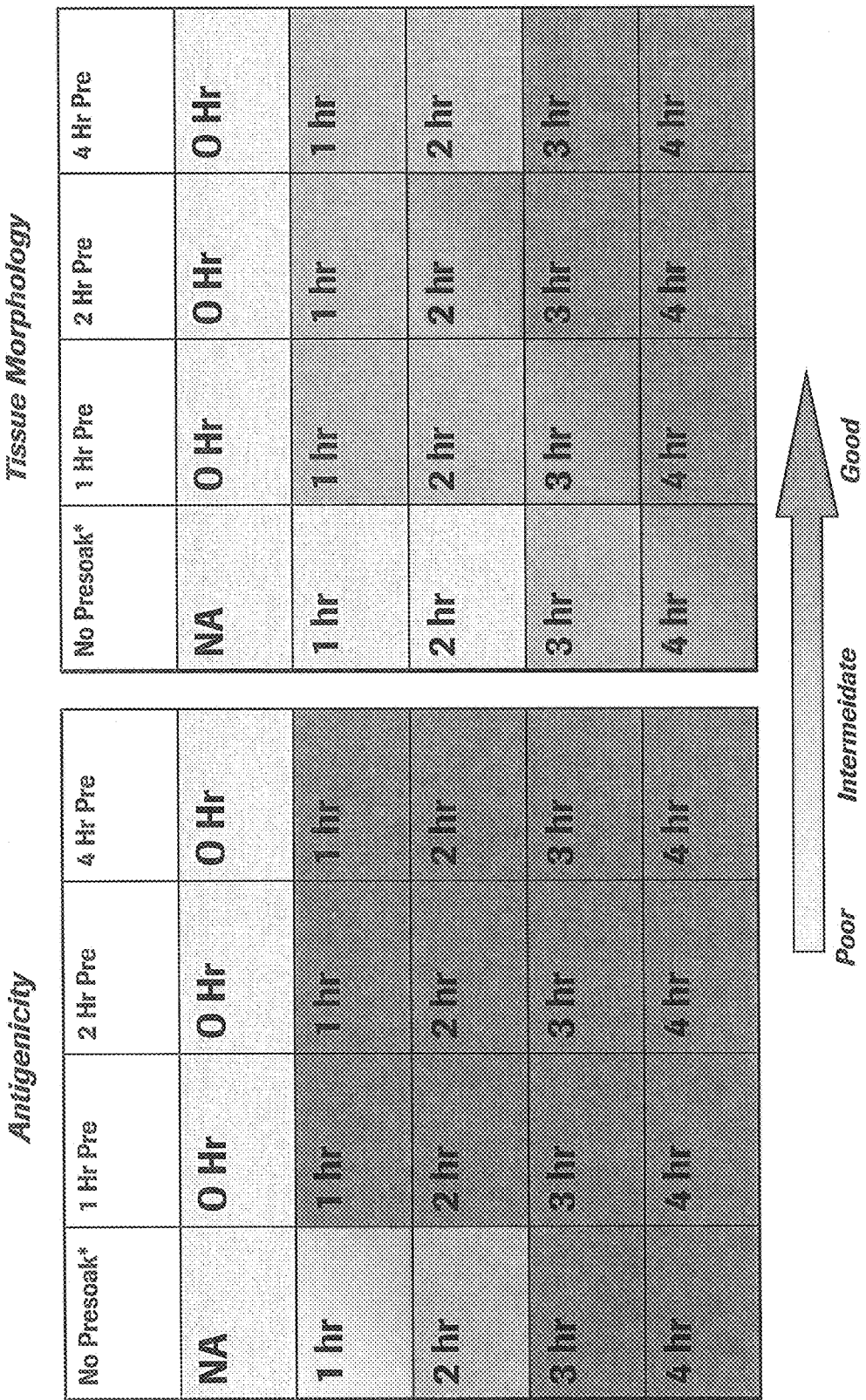
FIG. 10 is a is a graphical representation of antigenicity and tissue morphology results of tissue samples processed with varying pre-soak times compared to no pre-soak controls.

FIGS. 8-10 illustrate antigenicity and tissue morphology results obtained by considering different pre-soak times for samples treated in 10% formalin fixation solution at 4° C. for the amount of time indicated at the top of the graph, followed by tissue fixation at 45° C. for the time periods indicated in each cell. FIGS. 8-10 illustrate that a pre-soak of only 1 hour has a substantial benefit for antigenicity results, but that a 2-4 hour soak may be preferred for optimal tissue morphology results.

FIGS. 11A-E illustrate post-translation modification preservation by microscopic images of staining for pAKT on Calu-3 xenografts with different fixing protocols. Freshly harvested Calu-3 xenograft tumors were sliced into two roughly equal portions and treated with either 10% NBF (Formalin) at RT or 10% NBF at 4° C. Tumor samples treated with RT Formalin were placed directly into the solution within 5 minutes of tumor removal. Samples were then removed from the formalin at time intervals of 0 (A), 2 (B), 4 (C) or 24 (D) hours after submersion. One tumor sample was placed directly into formalin at 4° C. for 2 hours and then transferred to 45° C. formalin for an additional 2 hours (dual temperature fix protocol). Significantly more pAKT is retained indicated by the staining of anti-pAKT antibody in the present dual temperature fix protocol (2+2) (E) protocol than standard RT formalin processes (compare 24 hour (D) to 2+2 panels (E).

FIGS. 12A-D illustrate the signals observed in FIGS. 11A-E are indeed post-translation modification preservation by staining for pAKT on Calu-3 xenografts with (B and D) or without phosphate treatment (A and C). The specific staining by the antibody was abolished when treating samples with phosphate (B and D), indicating that the antibody is recognizing the phospho-moiety and is specific.

Figures 13A, 13B:
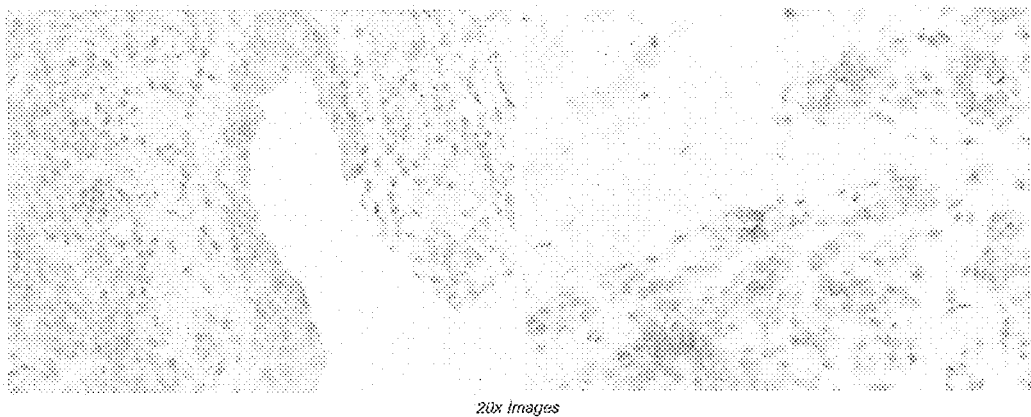
FIGS. 13A-B are microscopic images of staining for pAKT on human breast with ductal carcinoma in situ (DCIS).

FIGS. 13A-B illustrate post-translation modification preservation with the present dual temperature fix method (2+2; B) by staining pAKT with anti-pAKT antibody on human breast with ductal carcinoma in situ (DCIS). Significantly more pAKT is retained in the present dual temperature fix (2+2; B) protocol than standard RT formalin processes (compare 24 hour (A) to 2+2 panels). In addition, the staining appears much more specific for membranes in the present dual temperature fix protocol sample.

FIGS. 14A-D illustrate post-translation modification preservation with the present dual temperature fix method (2+3.5; B) by staining for pAKT with anti-pAKT antibody on Calu-3 xenografts. FIG. 14F is a graphical representation of quantitative analysis of positive staining for pAKT shown in FIGS. 14A-D. Significantly more pAKT is retained in the present dual temperature fix (2+3.5) sample than standard RT formalin processes (compare 24 hour to 2+3.5 panels). The first temperature soak at 4° C. is necessary to preserve phosphomarkers since the tumor sample placed directly into heated formalin without the first cold soak retained no staining with pAKT (0+3.5 panel).

FIGS. 15A-F illustrates degradation of post-translation signal after the sample was removed. Freshly harvested Calu-3 xenograft tumors were sliced into two roughly equal portions, wrapped in saline soaked gauze and placed on wet ice for 0 (A), 10 (B), 30 (C), 60 (D), 120 (E) or 240 (F) minutes. Each sample was then placed into 4° C. formalin for 2 hours and then transferred to 45° C. formalin for an additional 2 hours. The pAKT signal decreased significantly in 30 minutes post removal (C), even when cooled to 4° C. wet ice.

FIGS. 16A-I illustrate preservation of phosphomarkers of human colon carcinoma with the methods of the present invention (bottom panels). Samples were also stained with hematoxylin and eosin (top panels) for comparison of tissue morphology. FIGS. 16J and K are graphical representations of quantitative analysis of positive staining for pAKT or pPRAS40 in normal (red bars) and carcinoma (blue bars) cells under different fixing conditions. The slides were scanned for quantitation purposes using an Aperio slide scanner (Lower Picture). Pixels were binned into (four groups consisting of negative, weak positive, mid positive and strong positive) groups indicating positive (brown) or negative (blue). The percentage of positive pixels (sum of all positive pixels) is reported in the graph. Significantly more phosphomarker is retained in the present dual temperature fix (2+2) protocol than standard RT formalin processes (compare 24 hour to 2+2 panels). In addition, the samples undergoing intentional ischemia had significantly less retention of phosphomarkers than either the samples fixed by the present dual temperature fix protocol or samples fixed by the 24 hour temperature standard protocol.

Figure 17A:
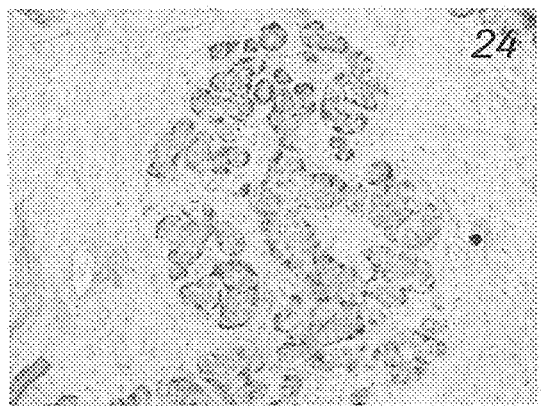
FIGS. 17A and B are microscopic images of staining for preservation of miRNA in human breast ductal carcinoma in situ (DCIS).
Figure 17B:
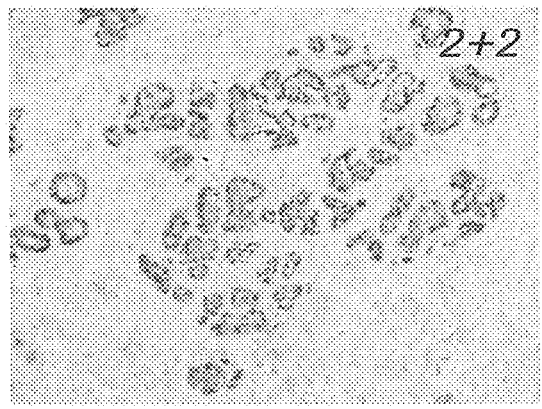

FIGS. 17A and B are microscopic images of staining for preservation of miRNA in human breast ductal carcinoma in situ (DCIS), breast tissue samples containing Ductal Carcinoma In Situ (DCIS) were preserved according to the present dual temperature fix protocol (2 hours 4° C. 10% NBF followed by 2 hours 45° C. 10% NBF) in comparison to those fixed by standard 24 hour room temperature formalin soak. The intensity of the miR205 staining (Intense Blue Signal) is clearly visible in both samples. The preservation of the 2+2 sample appears to be more intense than that of the standard control 24 hour fixed tissue.

Figure 18A:
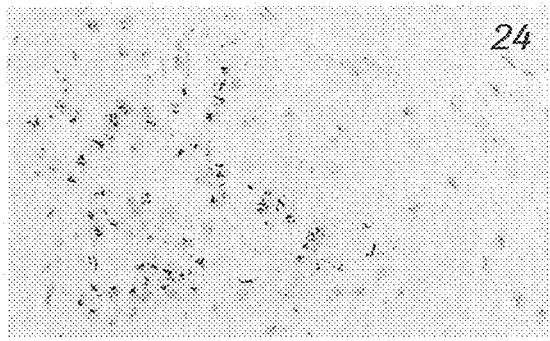
FIGS. 18A and B are microscopic images of staining for preservation of DNA in human breast ductal carcinoma in situ (DCIS).
Figure 18B:
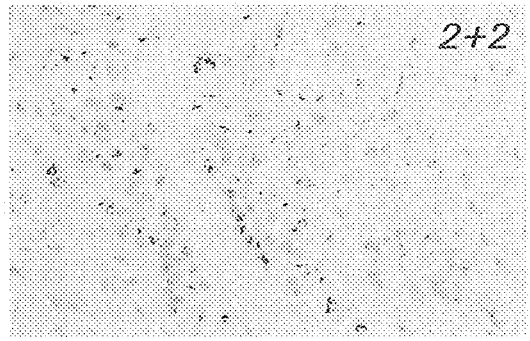

FIGS. 18A and B are microscopic images of staining for preservation of DNA in human breast ductal carcinoma in situ (DCIS) Ventana's dual ISH protocol (DDISH, Chromosome 17/HER2) was performed to test for the ability to detect single and multiple copies of two different DNA targets. Breast tissue samples containing Ductal Carcinoma In Situ (DCIS) were preserved according to the Ventana rapid fixation protocol (2 hours 4° C. 10% NBF followed by 2 hours 45° C. 10% NBF) in comparison to those fixed by standard 24 hour room temperature formalin soak. This illustrates that the present dual temperature fix protocol preserved the nucleic acid DNA in the tissue and could be detected by commercially available probes.

Figures 19A, 19B, 19C:
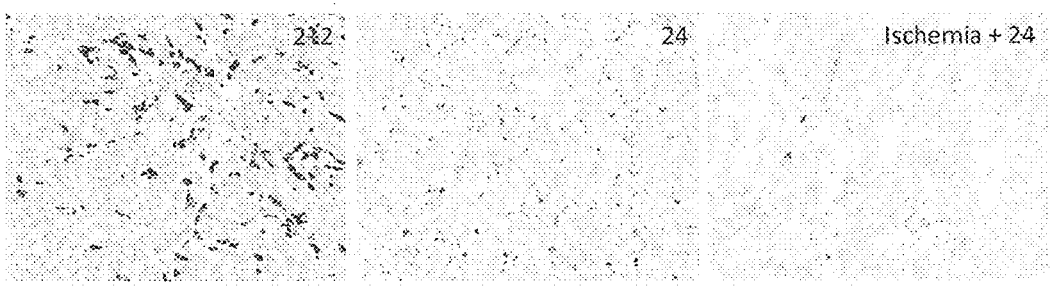
FIGS. 19A, B and C are microscopic images of staining for preservation of Hif1α on human colon carcinoma.

FIGS. 19A, B and C are microscopic images of staining for preservation of Hif1α on human colon carcinoma. A sample of a human colon was harvested and processed within 3-7 minutes of removal from the patient. Samples were sliced into roughly 4 mm pieces and treated with 3 different protocols. In Protocol 1, the sample was placed directly into formalin at 4° C. for 2 hours and then transferred to 45° C. formalin for an additional 2 hours (A). In protocol 2, the sample was placed into room temperature formalin for 24 hours after submersion (B). In protocol 3, the sample had purposeful ischemia for 1 hour prior to being placed into room temperature formalin for 24 hours (C). Significantly more Hif1α is retained in the present dual temperature fix (2+2) protocol than standard RT formalin processes (compare 24 hour to 2+2 panels). In addition, the samples undergoing purposeful ischemia had significantly less retention of Hif1α than either the samples fixed by the present dual temperature fix protocol (2+2) or samples fixed by the standard 24 hour fix protocol.

V. Use of the Present Invention:

The present invention can be used together with any of staining systems and protocols known in the art of traditional histochemistry, as well as immunohistochemistry and in situ hybridization. The present invention can also be used together with various automated staining systems, such as those marketed by Ventana Medical Systems, Inc., Tucson, Ariz., including the Benchmark XT, Benchmark Ultra, and Discovery automated platforms. Exemplary systems are disclosed in U.S. Pat. Nos. 6,352,861, 5,654,200, 6,582,962, 6,296,809, and 5,595,707, all of which are incorporated herein by reference.

The following description exemplifies a suitable embodiment of an automated method and system. Additional information concerning automated systems and methods also can be found in PCT/US2009/067042, which is incorporated herein by reference. Chromogenic detection facilitates visual unaided deciphering of patterns on the device.

In exemplary embodiments, detection is realized through anti-species antibodies conjugated with multiple enzymes (e.g. horse radish peroxidase (HRP), alkaline phosphatase (AP). This enzyme-antibody conjugate is referred to as an HRP or AP multimer in light of the multiplicity of enzymes conjugated to each antibody. Multimer technologies are described in U.S. application Ser. No. 12/687,564 which is hereby incorporated by reference in its entirety for disclosure related to antibody conjugates.

This type of detection chemistry technology is currently marketed by Ventana Medical Systems Inc., as ultraView Universal DAB detection kit (P/N 760-500), ultraView Universal AP Red detection kit (P/N 760-501), ultraView Red ISH DIG detection kit (P/N 760-505), and ultraView SISH DNP detection kit (P/N 760-098).

In illustrative embodiments, the approach uses non-endogenous haptens (e.g. not biotin, see U.S. application Ser. No. 12/660,017 which is hereby incorporated by reference in its entirety for disclosure related to detection chemistries). In illustrative embodiments, a tyramide signal amplification may be used with this approach to further increase the sensitivity and dynamic range of the detection (See PCT/US2011/042849 which is hereby incorporated by reference in its entirety for disclosure related to detection chemistries).

Any suitable enzyme/enzyme substrate system can be used for the disclosed fixation method. Working embodiments typically used alkaline phosphatase and horseradish peroxidase. If the enzyme is alkaline phosphatase, one suitable substrate is nitro blue tetrazolium chloride/(5-bromo-4-chloro-1H-indol-3-yl)dihydrogen phosphate (NBT/BCIP). If the enzyme is horseradish peroxidase, then one suitable substrate is diaminobenzidine (DAB). Numerous other enzyme-substrate combinations are known to those skilled in the art. For a general review of these, see U.S. Pat. Nos. 4,275,149, and 4,318,980. In some embodiments, the enzyme is a peroxidase, such as horseradish peroxidase or glutathione peroxidase or an oxidoreductase.

U.S. Patent Publication 2008/0102006, the entire disclosure of which is incorporated herein by reference, describes robotic fluid dispensers that are operated and controlled by microprocessors. U.S. Patent Publication 2011/0311123, the entire disclosure of which is incorporated herein by reference, describes methods and systems for automated detection of immunohistochemical (IHC) patterns. The automated detection systems disclosed in these patent applications can be used to detect the fixed tissue samples of the present invention.

EXAMPLES

The following examples are provided to illustrate certain features of working embodiments of the present invention.

A person of ordinary skill in the art will appreciate that the scope of the invention is not limited to the features recited in these examples.

Example 1

This example concerns a fixation time course for mouse kidney samples fixed at 30° C., 40° C., 50° C. and 60° C., and confirms previous results obtained with human tissue samples. Mouse kidneys were obtained fresh from the BMAC Department at Ventana Medical Systems, Inc.

20 ml. of formalin (10% NBF) were placed into 50 ml conical tubes. Tubes were placed into a standard VWR heat block set to either 30° C., 40° C., 50° C. or 60° C. Mouse kidneys were cut in half and three pieces were placed into each conical tube. One piece was removed after 10, 30 and 60 minutes of soak at each temperature.

Controls were conducted by placing mouse kidneys in room temperature formalin for 0, 2, 6 and 23 hours. All samples were processed in a Renaissance tissue processor (Ventana Medical Systems, Inc.; Catalog #V-REN) and embedded into paraffin wax blocks. Cut slides were stained with Gills II hematoxylin and Eosin Y for analysis of tissue morphology.

The 0 hour and 2 hour control tissues showed characteristic ethanol fixation properties. The 23 hour control was much better. The amount of fixation correlated with temperature and time. The 50° C. tissues approached the results obtained with the 23 hour control.

Example 2

This example concerns extended formalin heat soaks at 50° C., 60° C., 70° C., 80° C. and 90° C. to determine how much heat could be applied to the samples before the morphology or antigenicity suffered. Example 1 was repeated with the formalin soak, but human tonsil pieces were immersed in 10% NBF heated to 50° C., 60° C., 70° C., 80° C. and 90° C. Various time points were tried as illustrated below:

| | Soak Temperature | | | | |
|---|---|---|---|---|---|
| | 50° C. | 60° C. | 70° C. | 80° C. | 90° C. |
| Soak Minutes | 10 | 10 | 10 | 5 | 5 |
| | 30 | 30 | 30 | 10 | 10 |
| | 60 | 60 | 60 | 20 | 20 |
| | | | | 30 | 20 |

Slightly different time points were tried for 80° C. and 90° C. due to the extreme temperatures.

Tissue samples were immersed in 20 ml of 10% NBF heated to the temperatures described above. After appropriate times, pieces were removed to processing cassettes and stored in 70% ethanol. After all time points, tissues were processed in a standard tissue processor overnight. Tissues were sliced down the middle and embedded with the cut sides down (tissues sliced to expose the center).

For controls, pieces were soaked in 10% NBF at room temperature for 1, 2, 5 and 22 hours and processed like the experimental samples. All slides were stained with Gills II hematoxylin and Eosin Y. In addition, all slides were stained with antibodies Ki-67, CD34, Cyclin D1 and bcl-2.

Tissue Morphology Analysis: 50° C. and 60° C. blocks looked normal and correlated well with the time. 70° C. slides had decent tissue morphology with some evidence of heat-related anomalies. 80° C. and 90° C. blocks showed more evidence of heat artifacts. These included elongated cells near the edge of the tissue, pronounced rings around the germinal centers and chaotic cell structure with evidence of liquid movement or streaming.

IHC Analysis: The antigenicity of 50° C., 60° C., 70° C. and 80° C. blocks looked normal compared to controls at these short time points. At 90° C., most antibodies suffered decreased staining.

Fixation: The most pronounced effect on antigenicity occurred with the 0 hour unfixed control. Some antibodies were significantly decreased due to poor fixation conditions.

Example 3

This example concerns a pre-soak experiment where human tonsil pieces were pre-soaked in 10% NBF for 60 minutes prior to a soak in 52° C. formalin. The rationale was that the formalin would penetrate the tissue for the first hour but not much cross-linking would occur. Then the cross-linking reaction could be increased by raising the temperature.

An initial experiment was performed where human tonsil samples were soaked for 60 minutes at room temperature. The pieces were placed into pre-heated formalin for 10 minutes and processed into wax blocks. This showed a distinct ring pattern of fixation where the edges were well fixed but the middle was under fixed. This could be due to not enough pre-soak or insufficient time in the heated formalin.

To address these possibilities, a more complete experiment was performed. The soak times prior to fixation were extended and performed at 4° C.

| Pre-Soak Time (hours) at 4° C. | 0 | 1 | 2 |
|---|---|---|---|
| Soak at 50° C. in Minutes | 10 | 10 | 10 |
| | 30 | 30 | 30 |

Slides were stained with Gills II hematoxylin and Eosin Y.

Example 4

This example concerns pre-soak similar to Example 3 and performed on human tonsil tissue obtained from CHTN. This experiment was repeated many times due to the variable nature of examining different tonsil sections. Tonsil pieces were soaked in formalin in different ways. First, pieces were soaked in heated formalin, either 50° C. or 60° C., for 10, 30 and 60 minutes. The second mode was to first "pre-soak" the pieces in 4° C. formalin for 60 to 120 minutes prior to the heated step processing step.

| | | | | | | |
|---|---|---|---|---|---|---|
| Pre-Soak | 0 min. | 0 min. | 0 min. | 0 min. | 0 min. | 0 min. |
| 50° C. | 10 min. | 30 min. | 60 min. | | | |
| 60° C. | | | | 10 min. | 30 min. | 60 min. |
| Pre-Soak | 60 min. | 60 min. | 60 min. | 120 min. | 120 min. | 120 min. |
| 50° C. | 10 min. | 30 min. | 60 min. | | | |
| 60° C. | | | | 10 min. | 30 min. | 60 min. |

Slides were stained with Gills II hematoxylin and Eosin Y for tissue morphology.

In general, the slides not pre-soaked but simply subjected to 50° C. and 60° C. formalin showed incomplete fixation at the center of the tissues. The 60 minute soaks were close but not quite complete. The pieces that were pre-soaked for 1 or 2 hours at 4° C. then subjected to the heat profile were better, especially the 2 hour pre-soak, which was the preferred condition for these trials.

Example 5

This example concerns pre-soak Example 3. The results from Example 4 showed a preference for a pre-soak with formalin prior to a heated soak. The results of Example 4 were extended by using human tonsil and running a smaller, more focused experiment. For this experiment, a 120 minute, 4° C. formalin pre-soak was used with a 55° C. formalin cross-linking processing step.

| Pre-Soak | 0 min. | 0 min. | 0 min. | 120 min. | 120 min. | 120 min. |
|---|---|---|---|---|---|---|
| 55° C. | 10 min. | 30 min. | 60 min. | 10 min. | 30 min. | 60 min. |

Tissues were processed into paraffin blocks as usual in a Renaissance tissue processor (Ventana Medical Systems, Inc.; Catalog #V-REN) Slides were stained with Gills II hematoxylin and Eosin Y.

The results of this example confirmed that the 2 hour cold pre-soak with formalin provided the most even stains. 30 minutes of heated formalin may be a preferred minimum time for the heated soak.

Example 6

This example concerns pre-soaking at 4° C., 12° C. and 22° C. to determine what effects pre-soaking at various temperatures had on tissue morphology. Unfixed tissue samples were placed into formalin at 4° C., 12° C. and 22° C. for either 1 or 2 hours prior to heated formalin fixation.

For this experiment, two types of controls were performed. The first was a soak in room temperature formalin for 0 and 72 hours. The second control was a heated soak in 55° C. Formalin for 10, 30 and 60 minutes without a prior pre-soak.

Samples, either with or without pre-soak, were placed into 50 ml conical tubes containing 20 ml of formalin heated to 44° C. Tissues were removed after 10, 30 and 60 minutes, and placed into labeled tissue cassettes. Tissue cassettes were placed into a Leica tissue processor and an overnight program executed.

Tissue blocks were sectioned at 4 μm and stained with H & E to look at tissue morphology.

| Pre-soak Temp. | Pre-Soak Time | Formalin Soak | Formalin Soak Time |
|---|---|---|---|
| | | Room Temp. Formalin | 0 and 72 hours |
| | | 55° C. | 10, 30 and 60 min. |
| 4° C. | 1 hour | 55° C. | 10, 30 and 60 min. |
| | 2 hour | 55° C. | 10, 30 and 60 min. |
| 12° C. | 1 hour | 55° C. | 10, 30 and 60 min. |
| | 2 hour | 55° C. | 10, 30 and 60 min. |
| 22° C. | 1 hour | 55° C. | 10, 30 and 60 min. |
| | 2 hour | 55° C. | 10, 30 and 60 min. |

As expected, the 0 hour control had poor tissue morphology. The no pre-soak controls, subjected to 55° C. formalin, had poor tissue morphology as well. Any of the pre-soaked conditions seemed to work at the 60 minute, 55° C. condition. With lower times, the morphology was poor.

Example 7

This example concerns pre-soaking, but the tissue samples were fixed at 55° C. in a microwave tissue processor, which has a large formalin vessel (around 1 liter) as opposed to a 20 ml conical tube. The larger volume of formalin was not decreased in temperature nearly as much as the smaller volume. This may be important if transferring a piece from 4° C. to higher temperature fluid.

Samples of unfixed human tonsil were soaked in 55° C. formalin for various time periods. Some of the samples were subjected to a 2 hour pre-soak in 4° C. formalin prior to the 55° C. formalin.

For the heated formalin soak, the microwave tissue processor was used to pre-heat the formalin. Tissue cassettes were inserted into the multi-cassette holder and immersed into the heated formalin. At the appropriate times, one cassette was removed and placed into 70% ethanol for holding. When all cassettes were processed, they were further processed overnight into wax blocks.

Blocks were sectioned at 4 μm and stained with H & E for tissue morphology.

| Pre-Soak Temp. | Pre-Soak Time | Formalin Soak Temp. | Formalin Soak Time |
|---|---|---|---|
| | | Room Temp. | 0 hour |
| | | 55° C. | 10, 30 and 60 min. |
| 4° C. | 2 hours | 55° C. | 10, 30 and 60 min |

The results of this example demonstrate that pre-soaked samples were slightly better than presumed, especially in the middle.

Example 8

This example concerns using a pre-soak protocol on mouse kidney. Mouse kidneys were cut down the middle and an identical experiment was performed as in Example 6.

| Pre-Soak Temp. | Pre-Soak Time | Formalin Soak Temp. | Formalin Soak Time |
|---|---|---|---|
| | | Room Temp. | 0, 2, 4 and 24 hour |
| | | 55° C. | 10, 30 and 60 min. |
| 4° C. | 1 hour | 55° C. | 10, 30 and 60 min. |
| | 2 hour | 55° C. | 10, 30 and 60 min. |
| 12° C. | 1 hour | 55° C. | 10, 30 and 60 min. |
| | 2 hour | 55° C. | 10, 30 and 60 min. |
| 22° C. | 1 hour | 55° C. | 10, 30 and 60 min. |
| | 2 hour | 55° C. | 10, 30 and 60 min. |

The results of the experiment were. Mouse kidneys are smaller than the tonsil pieces used previously. Most of the heated formalin fixation conditions were acceptable.

Example 9

This example concerns fixation at 40° C., 55° C., 65° C. and 75° C. with or without pre-soak to explore the limits of how hot the formalin can be before detrimental effects on tissue are observed. Tissue sections were processed at 40° C., 55° C., 65° C. and 75° C. with and without a prior pre-soak in 4° C. formalin.

| Pre-Soak Temp. | Pre-Soak Time | Formalin Soak Temp. | Formalin Soak Time |
|---|---|---|---|
|  |  | Room Temp. | 0, 2, 4 and 24 hour |
| 4° C. | 2 hour | 40° C. | 10, 30 and 60 min. |
|  |  | 40° C. | 10, 30 and 60 min. |
| 4° C. | 2 hour | 55° C. | 10, 30 and 60 min. |
|  |  | 55° C. | 10, 30 and 60 min. |
| 4° C. | 2 hour | 65° C. | 10, 30 and 60 min. |
|  |  | 65° C. | 10, 30 and 60 min. |
| 4° C. | 2 hour | 75° C. | 10, 30 and 60 min. |
|  |  | 75° C. | 10, 30 and 60 min. |

Tissues were stained with H & E for tissue morphology. Tissues were also stained with bcl-2 and Cyclin D1 to check antigenicity results. Pre-soaked slides showed superior morphology as well as antigenicity. There was a drop off in antigenicity at 55° C. and above.

Example 10

This example concerns fixation at 40° C., 55° C. and 70° C. with or without pre-soak, in a manner very similar to Example 9. The only differences are the exact heated formalin temperatures, and the heated soak time was extended.

| Pre-Soak Temp. | Pre-Soak Time | Formalin Soak Temp. | Formalin Soak Time |
|---|---|---|---|
|  |  | Room Temp. | 0, 2, 4, 6, 8 and 24 hours |
| 4° C. | 2 hour | 40° C. | 10, 30, 60 and 90 min. |
|  |  | 40° C. | 10, 30, 60 and 90 min |
| 4° C. | 2 hour | 55° C. | 10, 30, 60 and 90 min |
|  |  | 55° C. | 10, 30, 60 and 90 min |
| 4° C. | 2 hour | 70° C. | 10, 30, 60 and 90 min |
|  |  | 70° C. | 10, 30, 60 and 90 min |

Tissues were stained with H & E to assess morphology. They were stained with bcl-2 and Cyclin D1 to assess antigenicity. The results of this example establish that tissue morphology acceptable at 40° C. and 55° C. for all time points. Some heat damage occurred at 70° C. for extended time treatments. Antigenicity decreased after about 1 hour at 55° C. and above. Antigenicity was stable at 40° C.

Example 11

This example concerns varying pre-soak times from 1 to 3 hours to investigate pre-soak time as a function of tissue morphology and antigenicity. Unfixed human tonsil samples were pre-soaked in 4° C. formalin for between 1 and 3 hours. Samples were fixed in 45° C. Formalin as indicated below:

| Pre-Soak Temp. | Pre-Soak Time | Formalin Soak Temp. | Formalin Soak Time |
|---|---|---|---|
|  |  | Room Temp. | 0, 2, 5 and 24 hour |
|  |  | 45° C. | 30, 60, 120 min |
| 4° C. | 1 hour | 45° C. | 30, 60, 120 min. |
| 4° C. | 2 hour | 45° C. | 30, 60, 120 min. |
| 4° C. | 3 hour | 45° C. | 30, 60, 120 min |

Tissue sections were cut at 4 μm and stained with H & E for tissue morphology. The tissue sections were also stained with bcl-2 for antigenicity. The results of this example were somewhat inconclusive. The tissue sections were not very large so the pre-soak time was adequate.

Example 12

This example concerns varying pre-soak times from 1 to 4 hours with substantially the same parameters used for Example 12, except that pre-soak times were varied to four hours, and the heated formalin soak was extended to 4 hours.

| Pre-Soak Temp. | Pre-Soak Time | Formalin Soak Temp. | Formalin Soak Time |
|---|---|---|---|
|  |  | Room Temp. | 0 and 24 hour |
|  |  | 45° C. | 1, 2, 3 and 4 hours |
| 4° C. | 1 hour | 45° C. | 0, 1, 2, 3 and 4 hours. |
| 4° C. | 2 hour | 45° C. | 0, 1, 2, 3 and 4 hours. |
| 4° C. | 4 hour | 45° C. | 0, 1, 2, 3 and 4 hours. |

Tissue sections were stained with bcl-2 to examine how well the antigenicity responded with pre-soak time. The pre-soak times did not matter much, but this seems largely due to the small size of the tissue samples. However, at the earliest time, 1 hour, there seemed to be a slight effect on both tissue morphology and antigenicity.

The results for various experiments, such as Example 12, are summarized in FIG. 8.

Example 13

This example concerns varying pre-soak times from 1 to 4 hours, as basically a repeat of Example 13 to increase the size of the tonsil sections being used.

| Pre-Soak Temp. | Pre-Soak Time | Formalin Soak Temp. | Formalin Soak Time |
|---|---|---|---|
|  |  | Room Temp. | 0 and 24 hour |
|  |  | 45° C. | 1, 2, 3 and 4 hours |
| 4° C. | 1 hour | 45° C. | 0, 1, 2, 3 and 4 hours. |
| 4° C. | 2 hour | 45° C. | 0, 1, 2, 3 and 4 hours. |
| 4° C. | 4 hour | 45° C. | 0, 1, 2, 3 and 4 hours. |

The above experiment was produced for two different sets of tissues and 43 blocks generated. The slides were stained with H & E for tissue morphology and bcl-2 for antigenicity. The results from this example are summarized by FIG. 9.

Example 14

This example concerns analyzing xylene soak times after NBF and ethanol.

| Pre-treatment | 70% | 95% | 100% | Xylene | Wax |
|---|---|---|---|---|---|
| Samples soaked in | 30 min. | 30 min. | 30 min. | 30 min. | 3 hours |
| 10% NBF at 4° C. | 30 min. | 30 min. | 30 min. | 60 min. | 3 hours |
| for 2 hours, then 2 |  |  |  |  |  |
| hours 45° C. fix |  |  |  |  |  |
| 24 hour, room | 30 min. | 30 min. | 30 min. | 30 min. | 3 hours |
| temperature fix | 30 min. | 30 min. | 30 min. | 60 min. | 3 hours |

For this example, tissue morphology for most tissues appeared normal. The samples soaked for only 15 minutes in xylene had muted germinal centers and the tissue appeared slightly pinker than control tissue. However, at 30 minutes of xylene clearing, tissues were good. So, for 2 mm thick, at least 30 minutes of xylene appears best.

Example 15

This example discusses staining for pAKT on Calu-3 Xenografts. In this example, freshly harvested Calu-3 xenograft tumors were sliced into two roughly equal portions and treated with either 10% NBF (Formalin) at RT or 10% NBF at 4 degrees C. Tumor samples treated with RT Formalin were placed directly into the solution within 5 minutes of tumor removal. Samples were then removed from the formalin at time intervals of 0, 2, 4 or 24 hours after submersion. One tumor sample was placed directly into formalin at 4° C. for 2 hours and then transferred to 45° C. formalin for an additional 2 hours. All samples were placed into 70% ethanol as a holding reservoir until being processed further in an automated tissue processor set to an overnight program. All samples were embedded into paraffin wax for microtomy. Slides were stained with an antibody recognizing pAKT epitope (Cell Signaling Technologies, Cat #4060) on an automated slide stainer (VENTANA Discovery XT instrument, Ventana Medical Systems, Inc.). As shown in FIGS. 11A-E, significantly more pAKT was retained in the present dual temperature fix (2+2) protocol than standard RT formalin processes (compare 24 hour to 2+2 panels).

Example 16

This example describes phosphatase treatment and staining for pAKT on Calu-3 Xenografts.

In this example, freshly harvested Calu-3 xenograft tumors were sliced into two roughly equal portions and treated with either 10% NBF (Formalin) at RT or 10% NBF at 4° C. Tumor samples treated with RT Formalin were placed directly into the solution within 5 minutes of tumor removal. Samples were then removed from the formalin after 24 hours (Top panel) after submersion. One tumor sample was placed directly into formalin at 4° C. for 2 hours and then transferred to 45° C. formalin for an additional 2 hours (Bottom Panel). All samples were placed into 70% ethanol as a holding reservoir until being processed further in an automated tissue processor set to an overnight program. All samples were embedded into paraffin wax for microtomy. After dewaxing the tissue specimen, the tissue was treated with lambda phosphatase and subsequently stained with an antibody recognizing pAKT epitope (Cell Signaling Technologies, Cat#4060) on an automated slide stainer (VENTANA Discovery XT instrument). As shown in FIGS. 12A-D, the specific staining by the antibody was abolished in both cases, indicating that the antibody is recognizing the phospho-moiety and is specific.

Example 17

This example describes staining for pAKT on human breast with ductal carcinoma In Situ (DCIS). In this example, a sample of a human breast was harvested and sliced into roughly 4 mm pieces and treated with either 10% NBF (Formalin) at RT or 10% NBF at 4° C. Tumor samples treated with RT Formalin were placed directly into the solution. Samples were then removed from the formalin at time intervals of 0, 2, 4 or 24 hours after submersion. One tumor sample was placed directly into formalin at 4° C. for 2 hours and then transferred to 45° C. formalin for an additional 2 hours. All samples were placed into 70% ethanol as a holding reservoir until being processed further in an automated tissue processor set to an overnight program. All samples were placed into 70% ethanol as a holding reservoir until being processed further in an automated tissue processor set to an overnight program. All samples were embedded into paraffin wax for microtomy. Slides were stained with an antibody recognizing pAKT epitope (Cell Signaling Technologies, Cat#4060) on an automated slide stainer (VENTANA Discovery XT instrument). As shown in FIGS. 13A and B, significantly more pAKT is retained in the present dual temperature fix (2+2) protocol than standard RT formalin processes (compare 24 hour to 2+2 panels). In addition, the staining appears much more specific for membranes in the samples fixed by the present dual temperature fix protocol.

Example 18

Figure 14A:
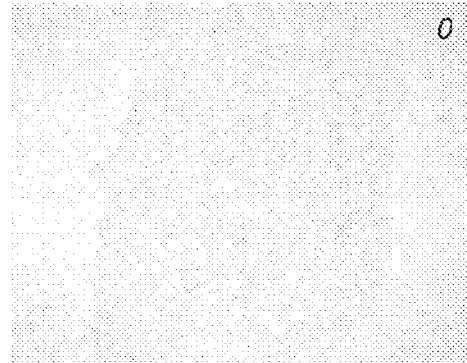
FIGS. 14A-D are microscopic images of staining for pAKT on Calu-3 xenografts under heat degradation.
Figure 14B:
Figure 14C:
Figure 14D:
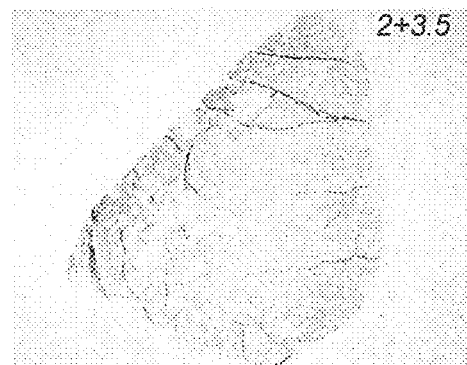
Figure 14E:
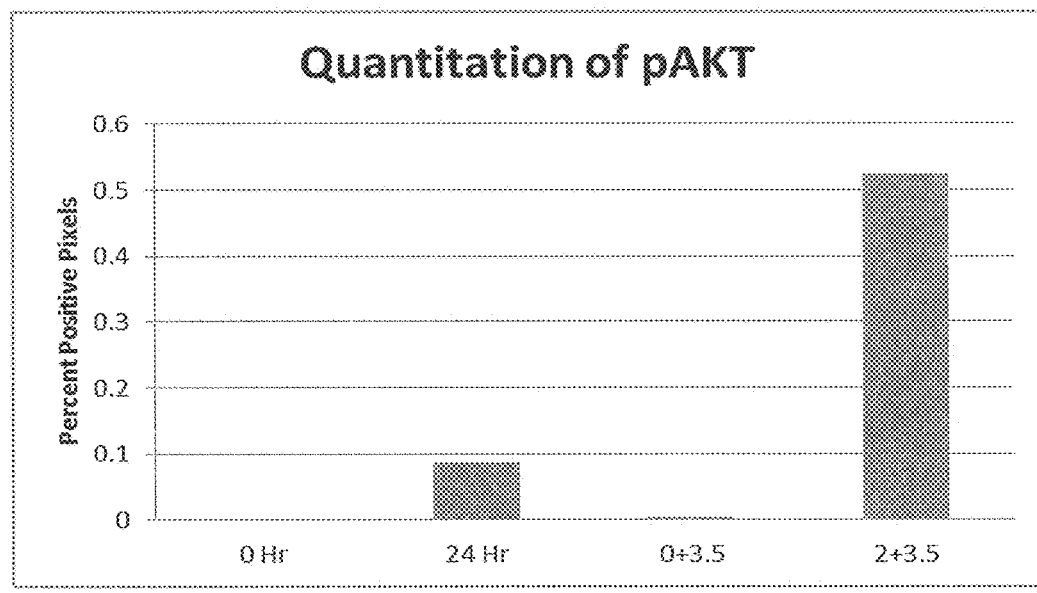
FIG. 14E is a graphical representation of quantitative analysis of positive staining for pAKT on Calu-3 xenografts under different conditions of heat degradation.
Figure 15A:
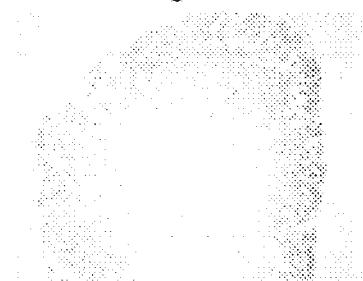
FIGS. 15A-F are microscopic images of staining for pAKT on Calu-3 xenografts showing degradation of post-translation signal after the sample was removed.
Figure 15B:
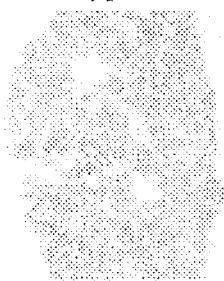
Figure 15C:
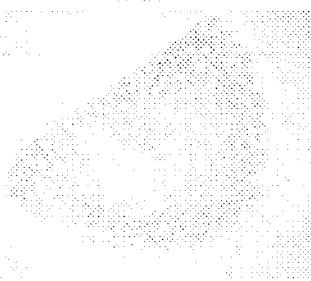
Figure 15D:
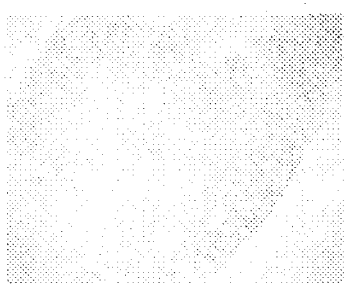
Figure 15E:
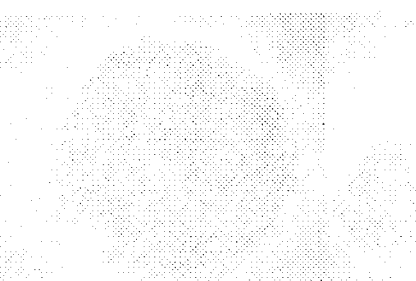
Figure 15F:
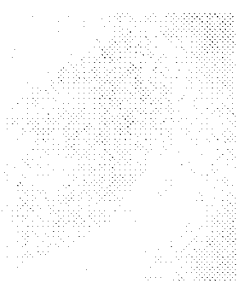
Figure 16J:
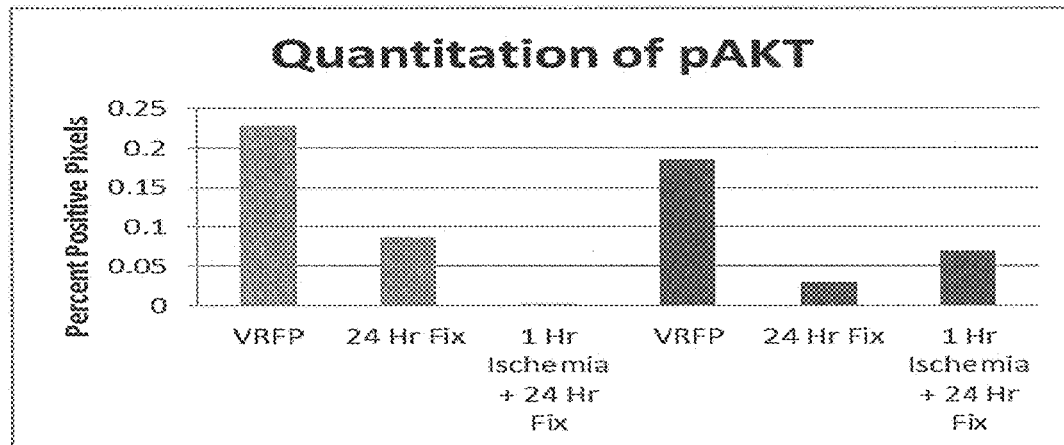
FIGS. 16J and K are graphical representations of quantitative analysis of positive staining for pAKT or pPRAS40 in normal and carcinoma cells under different fixing conditions.
Figure 16K:
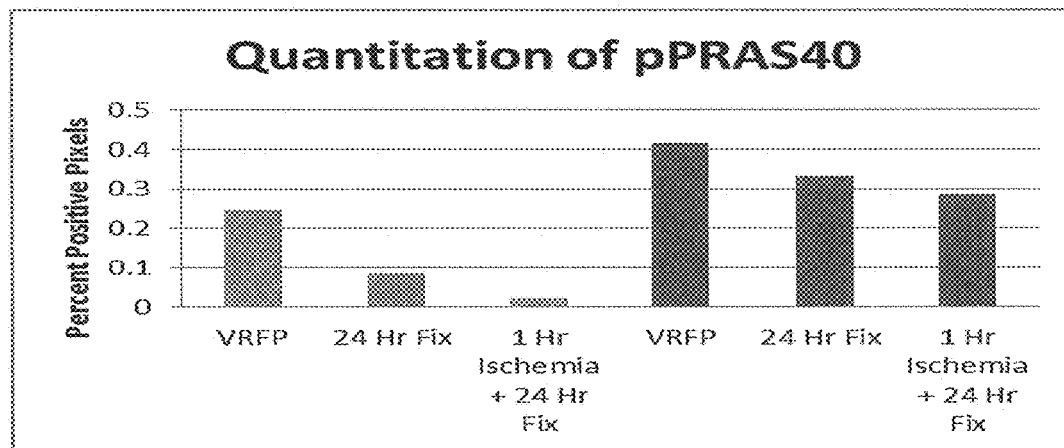
FIGS. 16A-I are microscopic images of staining for phosphomarkers on human colon carcinoma.

This example describes heat degradation of pAKT on Calu-3 Xenograft: In this example, freshly harvested Calu-3 xenograft tumors were sliced into two roughly equal portions and treated with either 10% NBF (Formalin) at RT or 10% NBF at 45° C. or 10% NBF at two different temperatures. Tumor samples treated with RT Formalin were placed directly into the solution within 5 minutes of tumor removal. Samples were then removed from the formalin at time intervals of 0 or 24 hours after submersion. One tumor sample was placed directly into formalin at 45° C. for 3.5 hours. Another tumor sample was placed in 4° C. formalin for 2 hours and then transferred to 45° C. formalin for an additional 2 hours. All samples were placed into 70% ethanol as a holding reservoir until being processed further in an automated tissue processor set to an overnight program. All samples were embedded into paraffin wax for microtomy. Slides were stained with an antibody recognizing pAKT epitope (Cell Signaling Technologies, Cat#4060) on an automated slide stainer (VENTANA Discovery XT instrument). As shown in FIGS. 14A-D, significantly more pAKT is retained in the (2+3.5) sample fixed by the present dual temperature fix protocol than standard RT formalin processes (compare 24 hour to 2+3.5 panels). The first temperature soak at 4° C. is necessary to preserve phospho-markers since the tumor sample placed directly into heated formalin without the first cold soak retained no staining with pAKT (0+3.5 panel). The slides were scanned for quantitation purposes using an Aperio slide scanner (Lower Picture). As shown in FIG. 14E, pixels were binned into two groups indicating positive (brown) or negative (blue). The percentage of positive pixels is reported in the graph.

Example 19

This example describes pAKT staining diminishes rapidly after removal. In this example, freshly harvested Calu-3 xenograft tumors were sliced into two roughly equal portions, wrapped in saline soaked gauze and placed on wet ice for 0, 10, 30, 60, 120 or 240 minutes. Each sample was then placed into 4° C. formalin for 2 hours and then transferred to 45° C. formalin for an additional 2 hours. All samples were placed into 70% ethanol as a holding reservoir until being processed further in an automated tissue processor set to an overnight program. All samples were embedded into paraffin wax for microtomy. Slides were stained with an antibody recognizing pAKT epitope (Cell Signaling Technologies, Cat#4060) on an automated slide stainer (VENTANA Discovery XT instrument). As shown in FIGS. 15A-F, pAKT signal decreased significantly in 30 minutes post removal (FIG. 15B), even when cooled to 4° C. on wet ice.

Example 20

This example describes staining for phosphomarkers on human colon carcinoma.

In this example, a sample of a human colon was harvested and processed within 3-7 minutes of removal from the patient. Samples were sliced into roughly 4 mm pieces and treated with 3 different protocols. In Protocol 1, the sample was placed directly into formalin at 4° C. for 2 hours and then transferred to 45° C. formalin for an additional 2 hours. In protocol 2, the sample was placed into room temperature formalin for 24 hours after submersion. In protocol 3, the sample had purposeful ischemia for 1 hour prior to being placed into room temperature formalin for 24 hours. All samples were placed into 70% ethanol as a holding reservoir until being processed further in an automated tissue processor set to an overnight program. All samples were placed into 70% ethanol as a holding reservoir until being processed further in an automated tissue processor set to an overnight program. All samples were embedded into paraffin wax for microtomy. Slides were stained with an antibody recognizing pAKT epitope (Cell Signaling Technologies, Cat#4060) or pPRAS40 epitotpe (Cell Signaling Technologies, Cat#) on an automated slide stainer (VENTANA Discovery XT instrument). As shown in FIGS. 16A-I, Significantly more phosphomarker is retained in the present dual temperature fix (2+2) protocol than standard RT formalin processes (compare 24 hour to 2+2 panels). In addition, the samples undergoing purposeful ischemia had significantly less retention of phosphomarkers than either the samples fixed by the present dual temperature fix protocol or samples fixed by 24 hour room temperature fix protocol. Samples were also stained with hematoxylin and eosin (top panels) for comparison of tissue morphology. The slides were scanned for quantitation purposes using an Aperio slide scanner (Lower Picture). Pixels were binned into two groups indicating positive (brown) or negative (blue). The percentage of positive pixels is reported in the graph.

Example 21

This example concerns the analysis of miRNA levels in samples fixed according to the present dual temperature fix protocol and standard protocols (24 hr.). miRNAs are short (21-25) nucleotides which act as post transcriptional modifiers of mRNA transcripts, influencing gene expression by preventing translation.

In this example, breast tissue samples containing Ductal Carcinoma In Situ (DCIS) were preserved according to the present dual temperature fix protocol(2 hours 4° C. 10% NBF followed by 2 hours 45° C. 10% NBF) in comparison to those fixed by standard 24 hour room temperature formalin soak. Slides were stained on a VENTANA Discovery Ultra automated slide stainer (Ventana Medical Systems, Inc.). Levels of miR205 in the samples were analyzed to determine what effect the present dual temperature fix protocol has on the retention and preservation of this particular miRNA. In this example, the intensity of the miR205 staining, an intense blue signal is clearly visible in both samples. As shown in FIGS. 17A and B, the preservation of the 2+2 sample appears to be more intense than that of the standard control 24 hour fixed tissue.

Example 22

This example concerns preservation of DNA in human breast ductal carcinoma in situ (DCIS).

In this example, HER2 Dual ISH DNA Probe Cocktails Chromosome 17/HER2 (DDISH; Ventana Medical System Inc. Catalog #780-4422),) was used in the breast tumor samples to test for the ability to detect single and multiple copies of two different DNA targets with the present dual temperature fix protocol. Breast tissue samples containing Ductal Carcinoma In Situ (DCIS) were preserved according to the present dual temperature fix protocol 2 hours 4° C. 10% NBF followed by 2 hours 45° C. 10% NBF) in comparison to those fixed by standard 24 hour room temperature formalin soak. The HER2 and Chromosome 17 probes were detected using two color chromogenic in situ hybridization (ISH) in the formalin-fix, paraffin embedded slides following staining on a VENTANA Discovery XT automated tissue stainer (Catalog #786-089) The HER2 gene status was then enumerated by calculating the ratio of the HER2 gene to Chromosome 17. As shown in FIGS. 18A and B, testing was successful for both samples, with single and multiple copies of the HER2 gene detected (Black signals). Additionally, Chromosome 17 centromere was successfully detected as well (Red signals). This illustrates that the present dual temperature fix protocol preserved the nucleic acid DNA in the tissue and could be detected by commercially available probes.

Example 23

This example describes staining for Hif1α on human colon carcinoma.

In this example, a sample of a human colon was harvested and processed within 3-7 minutes of removal from the patient. Samples were sliced into roughly 4 mm pieces and treated with 3 different protocols. In Protocol 1, the sample was placed directly into formalin at 4° C. for 2 hours and then transferred to 45° C. formalin for an additional 2 hours (A). In protocol 2, the sample was placed into room temperature formalin for 24 hours after submersion (B). In protocol 3, the sample had purposeful ischemia for 1 hour prior to being placed into room temperature formalin for 24 hours (C). All samples were placed into 70% ethanol as a holding reservoir until being processed further in an automated tissue processor set to an overnight program. All samples were embedded into paraffin wax for microtomy. Slides were stained with an antibody recognizing Hif1α epitope (ABCam, Cat# Ab51608) on an automated slide stainer (VENTANA Discovery XT instrument). As shown in FIGS. 19A, B and C, significantly more Hif1α is retained in the present dual temperature fix (2+2) protocol than standard RT formalin processes (compare 24 hour to 2+2 panels). In addition, the samples undergoing purposeful ischemia had significantly less retention of Hif1α than either the present dual temperature fix protocol (2+2) or 24 hour samples.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for fixing a tissue sample, consisting of:
    contacting the tissue sample with a first aldehyde solution for a first time period sufficient to diffuse the first aldehyde solution into an interior region of the tissue sample, a temperature of the first aldehyde solution during the first time period being from 0° C. to 10° C.; and removing the tissue sample from the first aldehyde solution that is in contact with the tissue sample during the first time period; and submerging the tissue sample in a second aldehyde solution preheated to a temperature from 22° C. to 50° C. for a second time period, the second time period being sufficient to fix the tissue sample.

2. The method according to claim 1, where the temperature of the first aldehyde solution during the first time period is from 3° C. to 5° C.

3. The method according to claim 1, where the first time period is from 15 minutes to 4 hours.

4. The method according to claim 1, where the first time period is from 1 hour to 2 hours.

5. The method according to claim 1, where the temperature of the second aldehyde solution during the second time period is from 35° C. to 45° C.

6. The method according to claim 1, where the second time period is from 1 hour to 4 hours.

7. The method according to claim 1, where the second time period is from 2 hours to 3 hours.

8. A method for fixing a tissue sample, consisting of:

immersing the tissue sample in a first formalin solution at a temperature from 0° C. to 5° C. for a first time period from 15 minutes to 4 hours; and after the first period of time, transferring the tissue sample from the first formalin solution to a second formalin solution at a temperature from 22° C. to 55° C. and immersing the tissue sample in the second formalin solution for a second time period from about 1 hour to about 4 hours.

9. The method according to claim 1, where the tissue sample is from 1 mm to 10 mm thick.

10. The method according to claim 8, where the tissue sample is from 1 mm to 10 mm thick.

11. The method according to claim 1, where the first time period is sufficient to diffuse the formalin solution throughout substantially all of the tissue sample.

12. The method according to claim 8, where the immersing the tissue sample in the second formalin solution includes immersing the tissue sample in the second formalin solution at a temperature from 35° C. to 45° C. for the second time period.

13. The method of claim 1, where at least 50% of post-translational modification signals within the tissue sample before contacting the tissue sample and the first aldehyde solution for the first time period are preserved after fixing the tissue sample for the second time period.

14. A method for processing a tissue sample, consisting of:

contacting the tissue sample and a first formalin solution at a temperature from 0° C. to 10° C. for a first time period sufficient to diffuse the first formalin solution throughout substantially all of the tissue sample to obtain a formalin diffused tissue sample;

transferring the formalin-diffused tissue sample to a second formalin solution, the second formalin solution being at a temperature from 35° C. to 45° C., and holding the formalin-diffused tissue sample in the second formalin solution for a second time period from 1 hour to 4 hours to obtain a fixed tissue sample; and immunohistochemically staining the fixed tissue sample, where the tissue sample is from 1 mm to 10 mm thick and at least 50% of post-translational modification signals within the tissue sample before contacting the tissue sample and the first formalin solution for the first time period are preserved after contacting the tissue sample and the second formalin solution for the second time period.

15. The method of claim 1, wherein the second time period is at least one hour.

* * * * *